US009885072B2

(12) United States Patent
DeAngelis et al.

(10) Patent No.: US 9,885,072 B2
(45) **Date of Patent: *Feb. 6, 2018**

(54) HIGH MOLECULAR WEIGHT HEPAROSAN POLYMERS AND METHODS OF PRODUCTION OF USE THEREOF

(71) Applicant: The Board of Regents of the University of Oklahoma, Norman, OK (US)

(72) Inventors: Paul L. DeAngelis, Edmond, OK (US); Phillip Pummill, Oklahoma City, OK (US); Regina C. Visser, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,683

(22) Filed: Mar. 23, 2017

(65) Prior Publication Data

US 2017/0198325 A1 Jul. 13, 2017

Related U.S. Application Data

(63) Continuation of application No. 14/624,354, filed on Feb. 17, 2015, now abandoned, which is a continuation of application No. 13/854,435, filed on Apr. 1, 2013, now Pat. No. 8,980,608.

(60) Provisional application No. 61/617,952, filed on Mar. 30, 2012.

(51) Int. Cl.
*C12N 9/10* (2006.01)
*C12P 19/26* (2006.01)

(52) U.S. Cl.
CPC ............ *C12P 19/26* (2013.01); *C12N 9/1051* (2013.01); *C12Y 204/01* (2013.01)

(58) Field of Classification Search
CPC .................................................... C12N 9/1051
USPC ...................................................... 435/252.3
See application file for complete search history.

(56) References Cited

U.S. PATENT DOCUMENTS

| | | | |
|---|---|---|---|
| 5,314,876 | A | 5/1994 | Lormeau et al. |
| 5,384,398 | A | 1/1995 | Lormeau et al. |
| 5,407,911 | A | 4/1995 | Yamamoto et al. |
| 5,446,090 | A | 8/1995 | Harris |
| 5,550,187 | A | 8/1996 | Rhee et al. |
| 5,672,662 | A | 9/1997 | Harris et al. |
| 5,756,553 | A | 5/1998 | Iguchi et al. |
| 5,827,937 | A | 10/1998 | Ågerup |
| 5,876,433 | A | 3/1999 | Lunn |
| 5,958,899 | A | 9/1999 | Zoppetti et al. |
| 6,120,536 | A | 9/2000 | Ding et al. |
| 6,156,373 | A | 12/2000 | Zhong et al. |
| 6,162,797 | A | 12/2000 | Zoppetti et al. |
| 6,214,966 | B1 | 4/2001 | Harris |
| 6,444,447 | B1 | 9/2002 | DeAngelis |
| 6,664,331 | B2 | 12/2003 | Harris et al. |
| 6,730,334 | B2 | 5/2004 | Zhao |
| 7,026,440 | B2 | 4/2006 | Bentley et al. |
| 7,244,270 | B2 | 7/2007 | Lesh |
| 7,291,673 | B2 | 11/2007 | Hubbell et al. |
| 7,307,159 | B2 | 12/2007 | De Angelis |
| 7,771,981 | B2 | 8/2010 | De Angelis |
| 8,088,604 | B2 | 1/2012 | De Angelis et al. |
| 8,237,021 | B2 | 8/2012 | Arnaut et al. |
| 8,361,478 | B2 | 1/2013 | Pau et al. |
| 8,399,736 | B2 | 3/2013 | Myer et al. |
| 8,580,290 | B2 | 11/2013 | DeAngelis |
| 8,980,608 | B2 | 3/2015 | DeAngelis et al. |
| 2002/0193516 | A1 | 12/2002 | Bucevschi et al. |
| 2003/0017131 | A1 | 1/2003 | Park et al. |
| 2004/0087488 | A1 | 5/2004 | Parent et al. |
| 2004/0197868 | A1 | 10/2004 | DeAngelis |
| 2005/0255562 | A1 | 11/2005 | Rosenberg et al. |
| 2006/0172967 | A1 | 8/2006 | Toida |
| 2006/0188966 | A1 | 8/2006 | DeAngelis |
| 2008/0226690 | A1 | 9/2008 | DeAngelis |
| 2010/0036001 | A1 | 2/2010 | DeAngelis |
| 2012/0108802 | A1 | 5/2012 | DeAngelis et al. |
| 2014/0107066 | A1 | 4/2014 | DeAngelis |

FOREIGN PATENT DOCUMENTS

| | | | |
|---|---|---|---|
| AU | 2002256501 | | 9/2008 |
| AU | 2008207616 | | 3/2012 |
| EP | 0544592 | A2 | 6/1993 |
| WO | 0027437 | A3 | 5/2000 |
| WO | 0180810 | A2 | 11/2001 |
| WO | 02089742 | A2 | 11/2002 |
| WO | 03029261 | A2 | 4/2003 |
| WO | 09014559 | A2 | 1/2009 |
| WO | 10030342 | A2 | 3/2010 |

OTHER PUBLICATIONS

May, B.J. et al.; "Complete Genomic Sequence of Pasteurella Multocida, Pm70," PNAS (2001), vol. 98, No. 6 pp. 3460-3465.
Townsend, K.M. et al.; "Genetic Organization of Pasteurella Multocida Cap Loci and Development of a Multiplex Capsular PCR Typing System," Journal of Clinical Microbiology, (2001), vol. 39, No. 3, pp. 924-929.
Hill, A.L., et al.; "Identification of the Xenopus Laevis cDNA for EXT1: A Phylogenetic Perspective," DNA Sequence (2002), vol. 13, No. 2, pp. 85-92; ISSN: 1042-5179; Taylor & Francis, Ltd.
Rimler, R.B.; "Presumptive Identification of Pasteurella Multocida Serogroups A, D and F by Capsule Depolymerisation with Mucopolysaccharidases"; Veterinary Record (1994), vol. 134, pp. 191-192.
Poggi., et al.; "Inhibition of B16-BL6 Melanoma Lung Colonies by Semisynthetic Sulfaminoheparosan Sulfates from *E. coli* K5 Polysaccharide," Seminars in Thrombosis and Hemostasis (2002), vol. 28, No. 4, pp. 383-391.
Kim, B.T., et al.; "Human Tumor Suppressor EXT Gene Family Members EXTL1 and EXTL3 Encode α1,4-N-Acetylglucosaminyltransferases That Likely Are Involved in Heparan Sulfate/Heparin Biosynthesis," PNAS (2001), vol. 98, No. 13, pp. 7176-7181.

(Continued)

*Primary Examiner* — Tekchand Saidha
(74) *Attorney, Agent, or Firm* — Dunlap Codding, P.C.

(57) ABSTRACT

High molecular weight heparosan polymers are described, as are methods of producing and using the high molecular weight heparosan polymers.

6 Claims, 10 Drawing Sheets
(8 of 10 Drawing Sheet(s) Filed in Color)

(56) References Cited

OTHER PUBLICATIONS

Vicenzi, E., et al.; "Broad Spectrum Inhibition of HIV-1 Infection by Sulfated K5 *Escherichia coli* Polysaccharide Derivatives," AIDS (2003) vol. 17, pp. 177-181; ISSN: 0269-9370 Lippincott Williams & Wilkins.

Lin, X, et al.: "Expression and Functional Analysis of Mouse EXT1, a Homolog of the Human Multiple Exostoses Type 1 Gene," Biochemical and Biophysical Research Communications (1998) vol. 248, No. 3, pp. 738-743.

Legeai-Mallet L., et al.; "EXT 1 Gene Mutation Induces Chondrocyte Cytoskeletal Abnormalities and Defective Collagen Expression in the Exostoses," Journal of Bone and Mineral Research (2000) vol. 15, No. 8, pp. 1489-1500.

McCormick, C., et al.; "The Putative Tumor Suppressor EXT1 Alters the Expression of Cell-Surface Heparan Sulfate," Nature Genetics (1998), vol. 19, No. 2, pp. 158-161.

Ahn, J., et al.; "Cloning of the Putative Tumour Suppressor Gene for Hereditary Multiple Exostoses (EXT1)," Nature Genetics (1995), vol. 11, No. 2, pp. 137-143.

Stickens, D., et al.; "The EXT2 Multiple Exostoses Gene Defines a Family of Putative Tumour Suppressor Genes," Nature Genetics (1996), vol. 14 pp. 25-32.

Simmons, A.D., et al.; "A Direct interaction Between EXT Proteins and Glycosyltransferases is Defective in Hereditary Mulitple Exostoses," Hum. Mol. Genet. (1999), vol. 8, No. 12, pp. 2155-2164.

Hagner-McWhirter A., et al.; "Biosynthesis of Heparin/Heparan Sulfate: Kinetic Studies of the Glucuronyl C5-Epimerase with N-Sulfated Derivatives of the *Escherichia coli* K5 Capsular Polysaccharide as Substrates," Glycobiology (2000) vol. 10, No. 2, pp. 159-171.

Lidholt, K., et al.; "Biosynthesis of Heparin. The D-Glucuronosyl- and N-Acetyl-D-Glucosaminyltransferase Reactions and their Relation to Polymer Modification," Biochem J. (1992), vol. 287, pp. 21-29.

Lin, X, et al.; "Disruption of Gastrulation and Heparan Sulfate Biosynthesis in EXT1-Deficient Mice," Developmental Biology (2000), vol. 224, pp. 299-311.

Van Hul, W., et al.; "Identification of a Third EXT-like Gene (EXTL3) Belonging to the EXT Gene Family," Genomics (1998), vol. 47, pp. 230-237.

Nader, H.B., et al.; "New Insights on the Specificity of Heparin and Heparan Sulfate Lyases from Flavobacterium Heparinum Revealed by the Use of Synthetic Derivatives of K5 Polysaccharide from *E. coli* and 2-0-Desulfated Heparin," Glycoconjugate Journal (1999), vol. 16, pp. 265-270.

DeAngelis, P.L., et al.; "Identification and Molecular Cloning of a Heparosan Synthase from Pasteurella Multocida Type D," The Journal of Biological Chemistry (2002) vol. 277, No. 9, ISSN: Mar. 1, pp. 7209-7213.

Naggi, A., et al.; "Toward a Biotechnological Heparin Through Combined Chemical and Enzymatic Modification of the *Escherichia coli* K5 Polysaccharide," Seminars in Thrombosis and Hemostasis (2001), vol. 27, No. 5, pp. 437-443.

Leali, D., et al.; "Fibroblast Growth Factor-2 Antagonist Activity and Angiostatic Capacity of Sulfated *Escherichia coli* K5 Polysaccharide Derivatives," The Journal of Biological Chemistry (2001) vol. 276, No. 41, pp. 37900-37908.

Duncan, G., et al.; "The Link Between Heparan Sulfate and Hereditary Bone Disease: Finding a Function for the EXT Family of Putative Tumor Suppressor Proteins," The Journal of Clinical Investigation (2001) vol. 108, No. 4, pp. 511-516.

Kim, B-T, et al.; "Demonstration of a Novel Gene DEXT3 of *Drosophila melanogaster* as the Essential N-Acetylglucosamine Transferase in the Heparan Sulfate Biosynthesis," The Journal of Biological Chemistry (2002) vol. 277, No. 16, pp. 13659-13665.

Sugahara, K., et al.; "Heparin and Heparan Sulfate Biosynthesis," Life (2002) vol. 54, pp. 163-175.

Lind, T., et al.; "Biosynthesis of Heparin/Heparan Sulfate," The Journal of Biological Chemistry (1993) vol. 268, No. 28, pp. 20705-20708.

Wei, G., et al.; "Location of the Glucuronosyltransferase Domain in the Heparan Sulfate Copolymerase EXT1 by Analysis of Chinese Hamster Ovary Cell Mutants," The Journal of Biological Chemistry (2000), vol. 275, No. 36, pp. 27733-27740.

Razz, N., et al.; "Structural and Functional Properties of Heparin Analogues Obtained by Chemical Sulphation of *Escherichia coli* K5 Capsular Polysaccharide," Biochem J. (1995) vol. 309, pp. 465-472.

Kusche, M., et al.; "Biosynthesis of Heparin—Use of *Escherichia coli* K5 Capsular Polysaccharide as a Model Substrate in Enzymic Polymer-Modification Reactions," Biochem J. (1991) vol. 275, pp. 151-158.

Casu, B., et al.; "Heparin-Like Compounds Prepared by Chemical Modification of Capsular Polysaccharide from *E. coli*," Elsevier Science Carbohydrate Research 263 (1994), pp. 271-284.

Vann, W.F., et al.; "The Structure of the Capsular Polysaccharide (K5 Antigen) of Urinary-Tract-Infective *Escherichia coli* 010:K5:H4," Eur. J. Biochem. (1981), vol. 116, pp. 359-364.

Toyoda, H., et al.; "Structural Analysis of Glycosaminoglycans in *Drosophila* and Caenorhabditis Elegans and Demonstrations That tout-velu, a *Drosophila* Gene Related to EXT Tumor Suppressors, Affects Heparan Sulfate in Vivo," The Journal of Biological Chemistry (2000), vol. 275, No. 4; pp. 2269-2275.

Zak, B.M., et al.; "Hereditary Multiple Exostoses and Heparan Sulfate Polymerization," Biochimica et Biophysica Acta 1573 (2002), pp. 346-355.

Katada, T., et al.; "cDNA Cloning and Distribution of XEXT1, the Xenopus Homologue of EXT1," Dev Genes Evol. (2002), vol. 212, pp. 248-250.

Kitagawa, H., et al.; "The Tumor Suppressor EXT-like Gene EXTL2 Encodes an $\alpha$1, 4-N-Acetylhexosaminyltransferase That Transfers N-Acetylgalactosamine and N-Acetylglucosamine to the Common Glycosaminoglycan-Protein Linkage Region," The Journal of Biological Chemistry (1999)m, vol. 274, No. 20, pp. 13933-139337.

Kitagawa, H., et al.; "Rib-2, a Caenorhabditis Elegans Homolog of the Human Tumor Suppressor EXT Genes Encodes a Novel $\alpha$1,4-N-Acetylglucosaminyltransferase Involved in the Biosynthetic Initiation and Elongation of Heparan Sulfate." The Journal of Biological Chemistry (2001) vol. 276, No. 7; pp. 4834-4838.

Song, G., et al.; "Identification of Mutations in the Human EXT1 and EXT2 Genes," Pub Med National Library of Medicine (1999), vol. 16. No. 4, pp. 208-210.

Clines, G.A., et al.; "The Structure of the Human Multiple Exostoses 2 Gene and Characterization of Homologs in Mouse and Caenorhabditis Elegans," Genome Research by Cold Spring Harbor Laboratory Press (1997) vol. 7, pp. 359-367, ISSN: 1054-9803/97.

Wise, C.A., et al.; "Identification and Localization of the Gene for EXTL, a Third Member of the Multiple Exostoses Gene Family," Genome Research by Cold Spring Harbor Laboratory Press (1997), vol. 7, pp. 10-16, ISSN: 1054-9803/97.

Linhardt, R.J., et al.; "Production and Chemical Processing of Low Molecular Weight Heparins," Seminars in Thrombosis and Hemostasis (1999), vol. 25, pages Suppl 3, pp. 5-16.

Fareed, J.; "Heparin, Its Fractions, Fragments and Derivatives—Some Newer Perspectives," Seminars in Thrombosis and Hemostasis, (1985), vol. 11, No. 1, 1985, pp. 1-9.

Lind, T., et al.; "The Putative Tumor Suppressors EXT1 and EXT2 Are Glycosyltransferases Required for the Biosynthesis of Heparan Sulfate.," The Journal of Biological Chemistry (1998) vol. 273, No. 41, pp. 26265-26268.

Senay, C., et al.; "The EXT1/EXT2 Tumor Suppressors: Catalytic Activities and Role in Heparan Sulfate Biosynthesis," EMBO Reports (2000) vol. 1, No. 3, pp. 282-286.

Bio Tie Therapies; BioHeparin "The Only Semi-synthetically Produced Low Molecular Weight Heparin," printed from www.biotie.com on Feb. 19, 2004. 7 pages.

Sasisekharan, R., et al.; "Heparin and Heparan Sulfate: Biosynthesis, structure and function," Current Opinion in Chemical Biology (2000), vol. 4, pp. 626-631.

(56) References Cited

OTHER PUBLICATIONS

Pedersen, L.C., et al.; "Heparan/Chondroitin Sulfate Biosynthesis.," The Journal of Biological Chemistry (2000), vol. 275, No. 44, pp. 34580-34585.
Finke, A., et al.; "Biosynthesis of the *Escherichia coli* K5 Polysaccharide, a Representative of Group II Capsular Polysaccharides: Polymerization in Vitro and Characterization of the Product," Journal of Bacteriology(1991), pp. 4088-4094.
Griffiths, G., et al.; "Characterization of the Glycosyltransferase Enzyme from the *Escherichia coli* K5 Capsule Gene Cluster and Identification and Charaterization of the Glucuronyl Active Site," The Journal of Biological Chemistry (1998), vol. 273, No. 19, pp. 11752-11757.
Hodson, N., et al.; "Identification That KfiA, a Protein Essential for the Biosynthesis of the *Escherichia coli* K5 Capsular Polysaccharide, Is an α-UDP-GlcNAc Glycosyltransferase," The Journal of Biological Chemistry (2000) vol. 275, No. 35, pp. 27311-27315.
Boyce, J.D., et al.; "Pasteurella Multocida Capsule: Composition, Function and Genetics," Journal of Biotechnology (2000), vol. 83, pp. 153-160.
Rimler, R.B., et al.; "Influence of Chondroitinase on Indirect Hemagglutination Titers and Phagocytosis of Pasteurella Multocida Serogroups A, D and F," Veterinary Microbiology (1995) vol. 47 pp. 287-294.
Rigg, G.P., et al.; "The Localization of KpsC, S and T, and KfiA, C and D Proteins Involved in the Biosynthesis of the *Escherichia coli* K5 Capsular Polysaccharide: Evidence for a Membrane-Bound Complex," Microbiology (1998), vol. 144, pp. 2905-2914.
DeAngelis, P.L., et al.; "Identification of the Capsular Polysaccharides of Type D and F Pasteurella Multocida as Unmodified Heparin and Chondroitin, Respectively," Carbohydrate Research (2002), vol. 337, pp. 1547-1552.
Jing, W., et al.; "Structure Function Analysis of Pasteurella Glycosaminoglycan Synthesis," Annual Conference of the Society for Glycobiology (188), p. 705.
McCormick, C., et al.; "The Putative Tumor Suppressors EXT1 and EXT2 Form a Stable Complex That Accumulates in the Golgi Apparatus and Catalyzes the Synthesis of Heparan Sulfate," PNAS ( 2000) vol. 97, No. 2, pp. 668-673.
Cheung, P.K., et al.; "Etiological Point Mutations in the Hereditary Multiple Exostoses Gene EXT1: A Functional Analysis of Heparan Sulfate Polymerase Activity," Am. J. Hum. Genet. (2001), vol. 69, pp. 55-66.
Wyatt Technology Corporation; "Heparin Characterization," Printed from www.tigc.org, on Apr. 5, 1997.
Soldani, G., et al.; "Experimental and Clinical Pharmacology of Glycosaminoglycans (GAGs)," Drugs Exptl. Clin. Res. (1991) vol. XVII, No. I, pp. 81-85.
Van Aken, H., et al.; "Anticoagulation: The Present and Future," Clin. Appl. Thrombosis/Hemostasis (2001) vol. 7 No. 3, pp. 195-204.
Lidholt, K., et al.; "Substrate Specificities of Glycosyltransferases Involved in Formation of Heparin Precursor and *E. coli* K5 Capsular Polysaccharides," Carbohydrate Research (1994), vol. 255, pp. 87-101.
Roberts, I., et al.; "Molecular Cloning and Analysis of Genes for Production of K5, K7, K12, and K92 Capsular Polysaccharides in *Escherichia coli*," Journal of Bacteriology (1986), vol. 168, No. 3, pp. 1228-1233.
Kröncke, K.D., et al.; "Expression of the *Escherichia coli* K5 Capsular Antigen: Immunoelectron Microscopic and Biochemical Studies with Recombinant *E. coli*," Journal of Bacteriology (1990), pp. 1085-1091.
Roberts, I.S., et al.; "Common Organization of Gene Clusters for Production of Different Capsular Polysaccharides (K Antigens) in *Escherichia coli*," Journal of Bacteriology (1988), pp. 1305-1310.
Petit, C., et al.; "Region 2 of the *Escherichia coli* K5 Capsule Gene Cluster Encoding Proteins for the Biosynthesis of the K5 Polysaccharide," Molecular Microbiology (1995), vol. 17, No. 4, pp. 611-620.
Smith, A.N., et al.; "Molecular Analysis of the *Escherichia coli* K5 kps Locus: Identification and Characterization of an Inner-Membrane Capsular Polysaccharide Transport System," Molecular Microbiology (1990), vol. 4, No. 11, pp. 1863-1869.
Bronner, D., et al.; "Synthesis of the K5 (group II) Capsular Polysaccharide in Transport-deficient Recombinant *Escherichia coli*," FEMS Microbiology Letters 113 (1993), pp. 273-284.
Pandit, K.K.; "Capsular Hyaluronic Acid in Pasteurella Multocida Type A and its Counterpart in Type D," Research in Veterinary Science (1993), No. 54, pp. 20-24.
Linhardt, R.J., et al.; "Isolation and Characterization of Human Heparin," Biochemistry (1992), vol. 31, No. 49, pp. 12441-12445, Abstract only.
DeAngelis, P.L.; "Microbial Glycosaminoglycan Glycosyltransferases," Glysobiology (2002) vol. 12, No. 1, pp. 9R-16R.
Otto, N.J., et al.; "Structure/Function Analysis of Pasteurella Multocida Heparosan Synthases," Journal of Biological Chemistry (2012), vol. 287, No. 10, pp. 7203-7212.
Ausubel et al.; "Hybridization Analysis of DNA Blots," Current Protocols in Molecular Biology (1993) Supplement 21 2.10-2.10. 16.
Chica, R.A., et al.; "Semi-Rational Approaches to Engineering Enzyme Activity: Combining the Benefits of Directed Evolution and Rational Design," Elsevier Current Opinion in Biotechnology (2005) vol. 16, pp. 378-384.
DeAngelis, P.L. et al.; "Identification of a Distinct, Cryptic Heparosan Synthase from Pasteurella Multocida Types A, D, and F," Journal of Bacteriology (2004) vol. 186, No. 24, pp. 8529-8532.
Esko, J.D. et al.; "Molecular Diversity of Heparin Sulfate," J. Clin. Invest. (2001), vol. 108, pp. 169-173.
Guo, H.H., et al.; "Protein Tolerance to Random Amino Acid Change," PNAS (2004) vol. 101, No. 25, pp. 9205-9210.
Hänfling, P., et al.; "Analysis of the Enzymatic Cleavage (β Elimination) of the Capsular K5 Polysaccharide of *Escherichia coli* by the K5-Specific Coliphage: a Reexamination," Journal of Bacteriology (1996) vol. 178, No. 15, pp. 4747-4750.
Jing, W., et al.; "Dissection of the Two Transferase Activities of the Pasteurella Multocida Hyaluronan Synthase: Two Active Sites Exist in One Polypeptide," Glycobiology (2000) vol. 10, No. 9, pp. 883-889.
Kane, T.A., et al.; "Functional Characterization of PmHS1, a Pasteurella Multocida Heparosan Synthase," Journal of Biol. Chem. (2006) vol. 281, No. 44, pp. 33192-33197.
Manzoni, M., et al.; "Production of K5 Polysaccharides of Different Molecular Weight by *Escherichia coli*," Journal of BioActive and Compatible Polymers (1996) vol. 11, pp. 301-311.
Peppas, N.A., et al.; "New Challenges in Biomaterials," Science (1994) vol. 263, pp. 1715-1720.
The Thrombosis Interest Group of Canada; "Practical Treatment Guidelines—Heparin." Printed from http://www.tigc.org, 7 pages.
Seffernick, J.L., et al.; "Melamine Deaminase and Atrazine Chlorohydrolase: 98 Percent Identical But Functionally Different," Journal of Bacteriology (2001) vol. 183, No. 8, pp. 2405-2410.
Witkowski, A., et al.; "Conversion of a β-Ketoacyl Synthase to a Malonyl Decarboxylase by Replacement of the Active-Site Cysteine with Glutamine," Biochemistry (1999) vol. 38, pp. 11643-11650.
Crawford, B.E., et al.; "Cloning, Golgi Localization, and Enzyme Activity of the Full-length Heparin/Heparan Sulfate-Glucuronic Acid C5-epimerase," Journal of Biol. Chem. (2001) vol. 276, No. 24, pp. 21538-21543.
Chavaroche et al.; "In Vitro Synthesis of Heparosan Using Recombinant Pasteurella Multocida Heparsan Synthase PmHS2," Applied Microbioligy Biotechnology (2010) vol. 85, pp. 1881-1891.
Chavaroche et al.; "Production Methods for Heparosan, a Precursor of Heparin and Heparan Sulfate," Carbohydrate Polymers ( 2013) vol. 93, pp. 38-48.
U.S. Appl. No. 13/855,046; Paul L. DeAngelis; Office Action dated Apr. 6, 2015.

(56) References Cited

OTHER PUBLICATIONS

Tsung, et al.; "Biodegradable Polymers in Drug Delivery Systems," Fundamentals and Applications of Controlled Release Drug Delivery, edited by J. Siepmann, R.A. Siegal, and M.J. Rathbone (2012), pp. 107-123.
Ambrosio, et al.; "Rheological Study on Hyaluronic Acid and Its Derivative Solutions," Journal of Macromolecular Science—Part A, Pure and Applied Chemistry (1999), vol. 7&8, pp. 991-1000.
Sismey-Ragatz, et al.; "Chemoenzymatic Synthesis with Distinct Pasteurella Heparosan Synthases, Monodisperse Polymers and Unnatural Structures," The Journal of Biological Chemistry (2007), vol. 282, No. 39, pp. 28321-28327.
U.S. Appl. No. 14/060,077; Paul L. DeAngelis, Office Action dated Aug. 26, 2015.
EP Application No. 13767739.9, DeAngelis, et al. filed Oct. 30, 2014; EPO Communication Pursuant to Rules 70(2) and 70a(2) EPC dated Mar. 31, 2016.
EP Application No. 13767739.9, DeAngelis, et al. filed Oct. 30, 2014; EPO Communication pursuant to Article 94(3) EPC, dated Oct. 25, 2016.
EP Application No. 13767739.9, DeAngelis, et al. filed Oct. 30, 2014; EPO Communication Under Rule (3) EPC dated Feb. 20, 2017.
EP Application No. 13767739.9, DeAngelis, et al.; filed Oct. 30, 2014; Extended European Search Report dated Mar. 11, 2016.
EP Application No. 13767739.9, DeAngelis, et al.; filed Oct. 30, 2014; Response to Communication Under Rules 70(2) and 70a(2) EPC filed Oct. 10, 2016.
EP Application No. 13767739.9, DeAngelis, et al.; filed Oct. 30, 2014; Response to Examination Report filed Dec. 2, 2016.

PmHS-opt3 37 ATGGGTACCTCACTGTTTAAACGTGCTACGGAACTTTTTAAAAGCGGAAACTACAAAGAT
Native pmHS 37 ATGGGTACCTCACTGTTTAAACGTGCTACAGAACTTTTTAAAAGCGGCAACTACAAAGAT PmHS-opt3 97 GCTCTTACATTGTACGAAAACATCGCCAAAATCTATGGCAGCGAATCTCTGGTTAAATAC
Native pmHS 97 GCTCTTACGTTGTACGAAAACATCGCCAAAATCTACGGAAGCGAATCTCTGGTTAAATAC PmHS-opt3 157 AACATCGATATCTGCAAGAAAAATATCACGCAATCAAAAAGCAACAAAATCGAAGAAGAT
Native pmHS 157 AACATCGATATCTGCAAGAAAAATATTACACAATCAAAAAGCAACAAAATCGAAGAAGAT PmHS-opt3 217 AACATCTCAGGAGAAAACAAATTTTCTGTTTCAATCAAAGATTTATATAACGAAATTAGC
Native pmHS 217 AACATCTCAGGCGAAAACAAATTTTCTGTTTCAATCAAAGATTTATATAACGAAATTAGC PmHS-opt3 277 AATTCTGAATTGGGCATCACAAAAGAACGGTTAGGCGCACCGCCTTTGGTGTCTATTATC
Native pmHS 277 AATTCTGAATTGGGCATCACAAAAGAACGGTTAGGAGCTCCGCCTTTGGTGTCTATTATC PmHS-opt3 337 ATGACATCACATAACACGGAAAAATTTATCGAAGCCAGCATCAACTCTCTGCTTTTACAG
Native pmHS 337 ATGACATCACATAACACGGAAAAATTTATCGAAGCCAGCATCAACTCTCTGCTTTTGCAG PmHS-opt3 397 ACATACAACAACCTTGAAGTCATCGTTGTGGATGATTACTCTACAGATAAAACGTTTCAA
Native pmHS 397 ACATACAACAACCTTGAAGTCATCGTTGTGGATGATTACTCTACAGATAAAACGTTTCAA PmHS-opt3 457 ATCGCTTCAAGAATCGCCAATTCAACAAGCAAAGTAAAAACGTTTCGCTTAAACAGCAAT
Native pmHS 457 ATCGCTTCAAGAATCGCCAATTCAACAAGCAAAGTAAAAACGTTTCGCTTAAACAGCAAC PmHS-opt3 517 TTGGGCACATACTTTGCTAAAAACACGGGCATCTTAAAAAGCAAAGGAGATATCATTTTC
Native pmHS 517 TTGGGAACATACTTTGCTAAAAACACGGGCATCTTGAAAAGCAAAGGAGATATCATTTTC PmHS-opt3 577 TTTCAGGATTCTGATGATGTCTGCCATCATGAAAGAATTGAACGCTGTGTAAATGCCTTG
Native pmHS 577 TTTCAGGATTCTGATGATGTCTGCCATCATGAAAGAATTGAACGCTGTGTAAATGCCTTG PmHS-opt3 637 CTGAGCAACAAAGATAATATTGCAGTCCGTTGCGCGTATTCTCGGATCAACCTGGAAACA
Native pmHS 637 CTGAGCAACAAAGATAATATTGCAGTCCGTTGCGCGTATTCTCGGATCAACCTGGAAACA PmHS-opt3 697 CAAAACATCATCAAAGTAAACGATAACAAATACAAATTGGGCCTGATTACGCTTGGAGTT
Native pmHS 697 CAAAACATCATCAAAGTAAACGATAACAAATACAAATTGGGCCTGATTACGCTTGGAGTT PmHS-opt3 757 TATCGTAAAGTGTTTAACGAAATCGGCTTTTTCAATTGTACAACGAAAGCCTCTGATGAT
Native pmHS 757 TATCGTAAAGTGTTTAACGAAATCGGCTTTTTCAATTGTACAACGAAAGCCTCTGATGAT PmHS-opt3 817 GAATTTTACCATAGAATCATCAAATACTATGGAAAAAATCGCATTAATAACCTGTTTCTG
Native pmHS 817 GAATTTTACCATAGAATCATCAAATACTATGGAAAAAATCGCATTAATAACCTGTTTCTG PmHS-opt3 877 CCGTTGTACTACAACACAATGCGTGAAGATTCATTATTTAGCGATATGGTCGAATGGGTA
Native pmHS 877 CCGTTGTACTACAACACAATGCGTGAAGATTCATTATTTAGCGATATGGTCGAATGGGTA PmHS-opt3 937 GATGAAAACAACATCAAACAAAAAACGTCAGATGCACGGCAGAACTACTTGCATGAATTT
Native pmHS 937 GATGAAAACAACATCAAACAAAAAACGTCAGATGCACGGCAGAACTACTTGCATGAATTT

FIGURE 1C

```
PmHS-opt3    997  CAAAAAATCCATAACGAACGTAAACTGAACGAACTTAAAGAAATTTTTAGCTTTCCGAGA
Native pmHS  997  CAAAAAATCCATAACGAACGTAAACTGAACGAACTTAAAGAAATTTTTAGCTTTCCGCGG

PmHS-opt3    1057 ATTCATGATGCGCTGCCTATCTCAAAAGAAATGTCTAAACTTTCAAACCCGAAAATCCCT
Native pmHS  1057 ATCCATGATGCGCTGCCTATCTCAAAAGAAATGTCTAAACTTTCAAACCCGAAAATCCCT

PmHS-opt3    1117 GTTTACATCAACATTTGCTCAATTCCGTCTCGCATCAAACAATTACAGTACACAATCGGA
Native pmHS  1117 GTTTACATCAACATCTGCAGCATTCCGTCTCGCATCAAACAATTACAGTATACAATTGGC

PmHS-opt3    1177 GTGTTGAAAAACCAGTGTGATCATTTTCATATCTACTTGGATGGCTATCCGGAAGTTCCT
Native pmHS  1177 GTGTTGAAAAACCAGTGTGATCATTTTCATATCTACTTGGATGGCTATCCGGAAGTTCCT

PmHS-opt3    1237 GATTTTATCAAAAAATTGGGAAACAAAGCAACGGTGATCAACTGCCAAAACAAAAACGAA
Native pmHS  1237 GATTTTATCAAAAAATTGGGAAACAAAGCAACGGTGATCAACTGCCAAAACAAAAACGAA

PmHS-opt3    1297 AGCATCAGAGATAACGGCAAATTTATCCTTTTAGAAAAATTGATCAAAGAAAACAAAGAT
Native pmHS  1297 AGCATCAGAGATAACGGCAAATTTATCCTTTTGGAAAAATTGATCAAAGAAAACAAAGAT

PmHS-opt3    1357 GGATACTACATCACATGTGATGATGATATTCGCTATCCTGCGGATTATATTAATACGATG
Native pmHS  1357 GGATACTACATCACATGTGATGATGATATTCGCTATCCTGCGGATTATATTAATACGATG

PmHS-opt3    1417 ATTAAGAAAATTAACAAATACAACGATAAAGCAGCGATCGGCCTGCATGGAGTTATCTTT
Native pmHS  1417 ATTAAGAAAATTAACAAATACAACGATAAAGCAGCGATCGGCCTGCATGGAGTTATCTTT

PmHS-opt3    1477 CCGTCTCGTGTGAACAAATACTTTTCAAGCGATCGGATCGTCTACAACTTTCAGAAACCT
Native pmHS  1477 CCGTCTCGTGTGAACAAATACTTTTCAAGCGATCGGATCGTCTACAACTTTCAGAAACCT

PmHS-opt3    1537 TTAGAAAACGATACAGCAGTAAACATCTTGGGCACAGGAACGGTCGCGTTTAGAGTATCA
Native pmHS  1537 TTGGAAAACGATACAGCAGTAAACATCTTGGGCACAGGAACGGTCGCGTTTAGAGTATCA

PmHS-opt3    1597 ATCTTTAACAAATTTTCTCTGTCAGATTTTGAACATCCGGGCATGGTTGATATCTACTTT
Native pmHS  1597 ATCTTTAACAAATTTTCTCTGTCAGATTTTGAACATCCGGGCATGGTTGATATCTACTTT

PmHS-opt3    1657 AGCATCCTGTGCAAGAAAAATAACATCCTTCAAGTGTGTATCTCAAGACCTAGCAATTGG
Native pmHS  1657 AGCATCCTGTGCAAGAAAAATAACATCCTTCAAGTGTGTATCTCAAGACCTAGCAATTGG

PmHS-opt3    1717 CTGACAGAAGATAACAAAAACACAGAAACGCTTTTTCATGAATTTCAAAACCGCGATGAA
Native pmHS  1717 CTGACAGAAGATAACAAAAACACAGAAACGCTTTTTCATGAATTTCAAAACCGCGATGAA

PmHS-opt3    1777 ATCCAGAGCAAACTTATCATCTCTAACAACCCGTGGGGATATTCTTCAATCTACCCTTTG
Native pmHS  1777 ATCCAGAGCAAACTTATCATCTCTAACAACCCGTGGGGATACTCTTCAATCTACCCTTTG

PmHS-opt3    1837 CTGAACAACAACGCAAACTACTCAGAACTGATCCCGTGTCTTAGCTTTTATAACGAATAA
Native pmHS  1837 CTGAACAACAACGCAAACTACTCAGAACTGATCCCGTGTCTTAGCTTTTATAACGAATAA
```

FIGURE 1C (continued)

HIGH MOLECULAR WEIGHT HEPAROSAN POLYMERS AND METHODS OF PRODUCTION OF USE THEREOF

CROSS-REFERENCE TO RELATED APPLICATIONS/INCORPORATION BY REFERENCE STATEMENT

This application is a continuation of U.S. Ser. No. 14/624,354, filed Feb. 17, 2015, now abandoned; which is a divisional of U.S. Ser. No. 13/854,435, filed Apr. 1, 2013, now U.S. Pat. No. 8,980,608, issued Mar. 17, 2015; which claims benefit under 35 USC § 119(e) of U.S. provisional application Ser. No. 61/617,952, filed Mar. 30, 2012. The entire contents of the above-referenced patents and patent applications are hereby expressly incorporated herein by reference.

STATEMENT REGARDING FEDERALLY SPONSORED RESEARCH OR DEVELOPMENT

Not Applicable.

BACKGROUND

1. Field of the Inventive Concept(s)

The presently disclosed and/or claimed inventive concept(s) relates to methodology for the production and uses of glycosaminoglycan compositions, and more particularly, to compositions comprising an isolated heparosan polymer of high molecular weight, as well as methods of production and uses thereof.

2. Description of the Related Art

Biomaterials (loosely defined as compounds or assemblies that are used to augment or substitute for components of natural tissues or body parts) are and will continue to be integral components of tissue engineering and regenerative medicine approaches. Complex procedures including transplants and stem cell therapies promise to enhance human health, but limited supplies of donor organs/tissues and the steep learning curves (as well as ethical debates) for pioneering approaches are obstacles. There is a growing demand for more routine applications of biomaterials, such as in reconstructive surgery, cosmetics, and medical devices. Therefore, there is a need in the art for new and improved biomaterials that may be used, for example but not by way of limitation, for dermal filler applications and for surface coatings for implanted devices.

Hyaluronan (HA), poly-L-lactic acid (poly[lactide]), calcium hydroxyapatite and collagen based products dominate the current market for biomaterials utilized in reconstructive surgery and cosmetic procedures. However, these products have a number of undesirable properties for which manufacturers and healthcare professionals are seeking improvements. These disadvantages include, but are not limited to, limited lifetime, potential for immunogenicity and/or allergenicity, and non-natural appearance in aesthetic procedures. For enhancing biocompatibility and durability of an implanted device, HA, heparin, bovine serum albumin, pyrolytic carbon, or lipid coatings are employed to enhance biocompatibility of stents, catheters, and other implanted material devices. However, these products often cause fouling, clogging, or thrombus formation due to reactivity with the human body. Therefore, there is a need in the art for new and improved biomaterial compositions that overcome the disadvantages and defects of the prior art.

There are numerous medical applications of HA. For example, HA has been widely used as a viscoelastic replacement for the vitreous humor of the eye in ophthalmic surgery during implantation of intraocular lenses in cataract patients. HA injection directly into joints is also used to alleviate pain associated with arthritis. Chemically cross-linked gels and films are also utilized to prevent deleterious adhesions after abdominal surgery. Other researchers using other methods have demonstrated that adsorbed HA coatings also improve the biocompatibility of medical devices such as catheters and sensors by reducing fouling and tissue abrasion.

The presently disclosed and/or claimed inventive concept(s) overcomes the disadvantages and defects of the prior art. The presently disclosed and/or claimed inventive concept(s) is based on a biomaterial comprising heparosan, the natural biosynthetic precursor of heparin and heparan sulfate. This composition has numerous characteristics that provide improvements and advantages over existing products. While heparosan is very similar to HA and heparin, the molecule has greater stability within the body since it is not the natural final form of this sugar and therefore the body has no degradation enzymes or binding proteins that lead to loss of functionality. This property also reduces biofouling, infiltration, scarring and/or clotting. Heparosan is also more hydrophilic than synthetic coatings such as plastics or carbon. Finally, aside from bacterial HA, most other current filler biomaterials are typically animal-derived, which causes concern for side effects such as allergic reactions or stimulating granulation, and such side effects will not be a concern with heparosan. Also, most naturally occuring heparosan polymers are known to have certain size ranges of molecular weight, depending on origin of the heparosan biopolymer such as the biosynthesis pathways utilized, including types of catalysts, hosts, and supporting appratus. As is known in the art, the size distribution of the heparosan biopolymer affects its physical properties, such as viscosity, chain entanglement, and solubility. In the presently disclosed and/or claimed inventive concept(s), we have developed a means to produce extremely high molecular weight (MW) heparosan polymers that have higher viscosity and can be used at lower concentrations (either with or without chemical crosslinking) than the naturally occurring heparosan preparations.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1C contains an alignment of a *Bacillus* gene-optimized sequence (SEQ ID NO:11) with the native *Pasteurella multocida* heparosan synthase gene (SEQ ID NO:1).

DETAILED DESCRIPTION

Figure 1A:
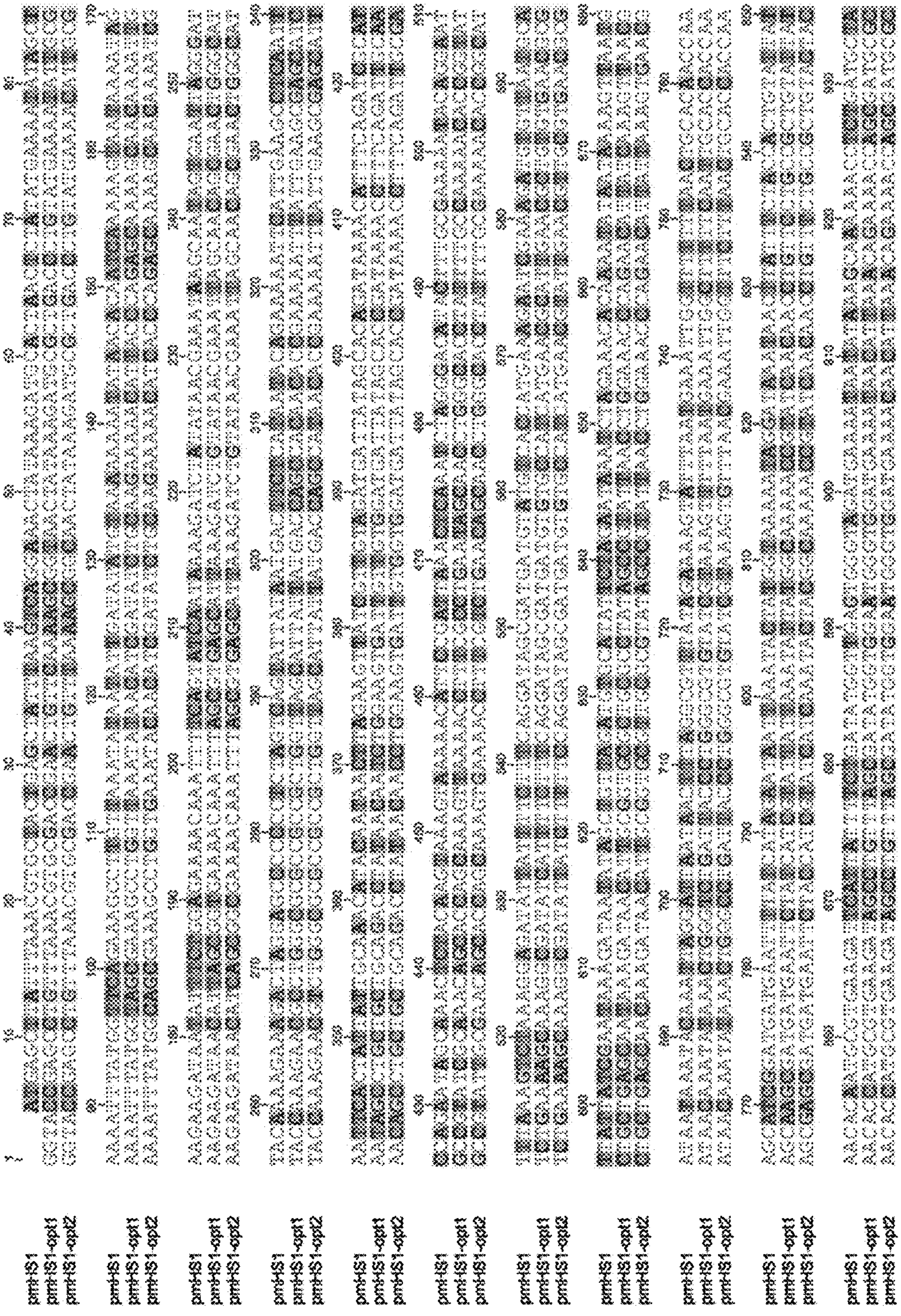
FIG. 1A contains an alignment of two *E. coli* gene-optimized sequences (SEQ ID NOS: 9 and 10) with the native *Pasteurella multocida* heparosan synthase gene (SEQ ID NO:1).
Figure 1A:
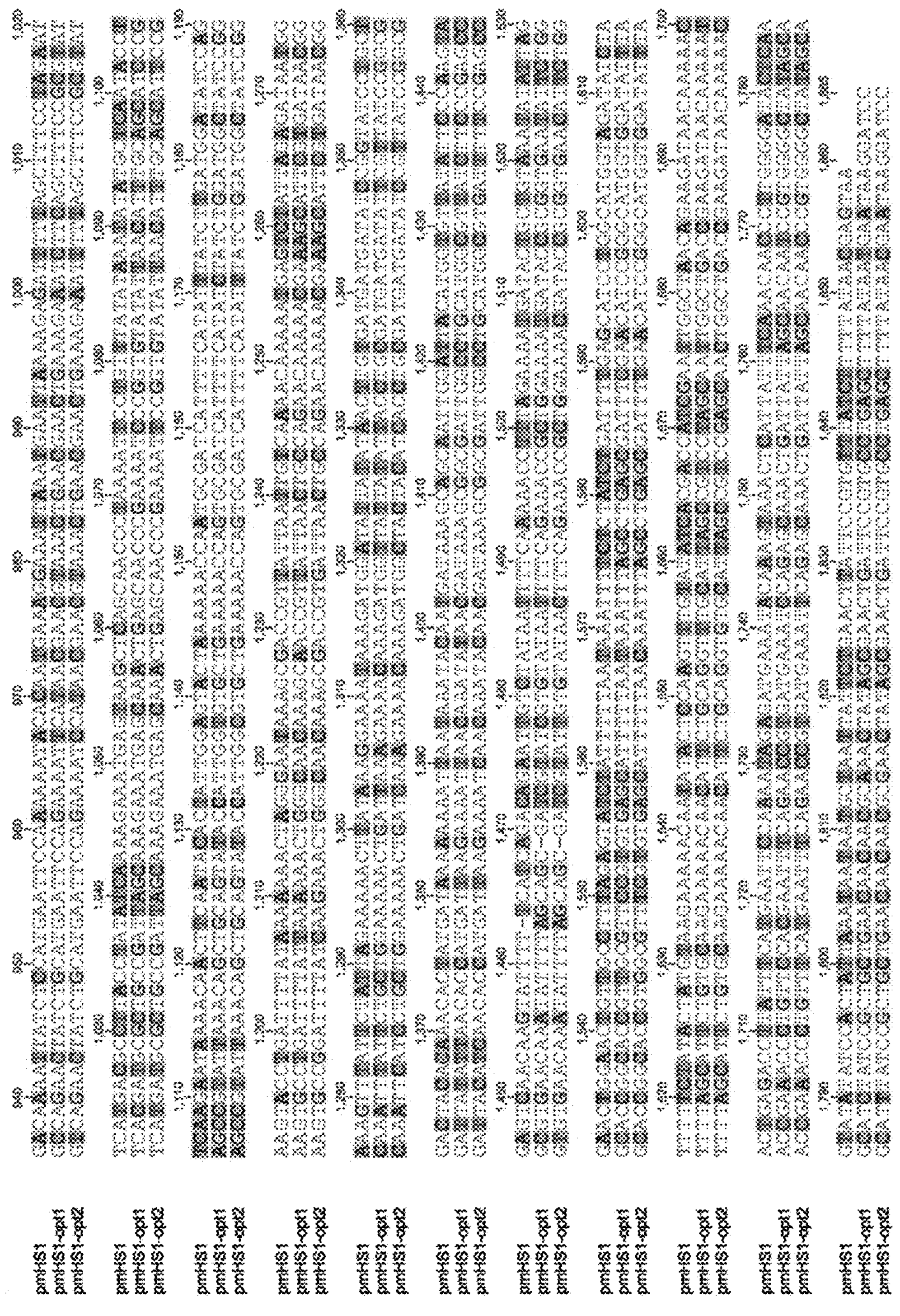

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and/or claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

Throughout the specification and claims, unless the context requires otherwise, the terms "substantially" and "about" will be understood to not be limited to the specific terms qualified by these adjectives/adverbs, but will be understood to indicate a value includes the inherent variation of error for the device, the method being employed to determine the value and/or the variation that exists among study subjects. Thus, said terms allow for minor variations and/or deviations that do not result in a significant impact thereto. For example, in certain instances the term "about" is used to indicate that a value includes the inherent variation of error for the device, the method being employed to determine the value and/or the variation that exists among study subjects. Similarly, the term "substantially" may also relate to 80% or higher, such as 85% or higher, or 90% or higher, or 95% or higher, or 99% or higher, and the like.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring. Similarly, a sugar polymer or polysaccharide with instrinsic structural features (such as but not limited to, composition, molecular weight (MW) distribution, etc.) found in native organisms (i.e., unmodified by the hand of man) is termed "naturally occurring".

The term "patient" as used herein includes human and veterinary subjects. "Mammal" for purposes of treatment refers to any animal classified as a mammal, including human, domestic and farm animals, nonhuman primates, and any other animal that has mammary tissue.

The terms "administration" and "administering", as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the presently disclosed and/or claimed inventive concept(s) (and/or the methods of administration of same) may be designed to provide delayed, controlled or sustained release using formulation techniques which are well-known in the art.

The term "dermal augmentation" in the context of the presently disclosed and/or claimed inventive concept(s) refers to any change of the natural state of a mammal's skin and related areas due to external acts. The areas that may be changed by dermal augmentation include, but not limited to, epidermis, dermis, subcutaneous layer, fat, arrector pill muscle, hair shaft, sweat pore, and sebaceous gland.

As used herein, the term "heparosan" will be understood to refer to the natural biosynthetic precursor of heparin and heparin sulfate. The sugar polymer heparosan is an unsulfated, unepimerized heparin molecule, and may also be referred to as "N-acetyl heparosan".

The term "tissue" as used herein will be understood to refer to a grouping of cells within an organism that are similarly characterised by their structure and function.

The term "biomaterial" as used herein will be understood to refer to any nondrug material that can be used to treat, enhance, protect, or replace any tissue, organ, or function in an organism. The term "biomaterial" also refers to biologically derived material that is used for its structural rather than its biological properties, for example but not by way of limitation, to the use of collagen, the protein found in bone and connective tissues, as a cosmetic ingredient, or to the use of carbohydrates modified with biotechnological processes as lubricants for biomedical applications or as bulking agents in food manufacture. A "biomaterial" is any material, natural or man-made, that comprises whole or part of a living structure or biomedical device that performs, augments, protects, or replaces a natural function and that is compatible with the body.

As used herein, when the term "isolated" is used in reference to a molecule, the term means that the molecule has been removed from its native environment. For example, a polynucleotide or a polypeptide naturally present in a living organism is not "isolated," but the same polynucleotide or polypeptide separated from the coexisting materials of its natural state is "isolated." Further, recombinant DNA molecules contained in a vector are considered isolated for the purposes of the presently disclosed and/or claimed inventive concept(s). Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Overall, this also applies to carbohydrates in general. Thus, not all "isolated" molecules need be "purified."

As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified.

As used herein, the term "substantially purified" refers to a compound that is removed from its natural environment and is at least 60% free, preferably 75% free, and most preferably 90% free from other components with which it is naturally associated.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, such as more than about 85%, 90%, 95%, and 99%. In one embodiment, the object species is purified to essential homogeneity (contaminant species cannot be detected in the composition by conventional detection methods) wherein the composition consists essentially of a single macromolecular species.

As used herein, the term "substrate" will be understood to refer to any surface of which a coating may be disposed. Examples of substrates that may be utilized in accordance with the presently disclosed and/or claimed inventive concept(s) include, but are not limited to, silica, silicon, glass, polymers, nanotubes, nanoparticles, organic compounds, inorganic compounds, metals and combinations thereof. When the substrate is a metal, the metal may include, but is not limited to, gold, copper, stainless steel, nickel, aluminum, titanium, thermosensitive alloys and combinations thereof.

The terms "gel" and "semi-solid" are used interchangeably herein and will be understood to include a colloidal system, with the semblance of a solid, in which a solid is dispersed in a liquid; the compound may have a finite yield stress. The term "gel" also refers to a jelly like material formed by the coagulation of a colloidal liquid. Many gels have a fibrous matrix and fluid filled interstices: gels are viscoelastic rather than simply viscous and can resist some mechanical stress without deformation. When pressue is applied to gels or semi-solids, they conform to the shape at which the pressure is applied.

The term "hydrogel" is utilized herein to describe a network of polymer chains that are water-insoluble, sometimes found as a colloidal gel in which water is the dispersion medium. Hydrogels are very absorbent natural or synthetic polymers, and may contain over 99% water. Hydrogels also possess a degree of flexibility very similar to natural tissue, due to their significant water content. In addition, peptides and/or larger biologically active substances can be enclosed in hydrogels, thereby forming a sustained release composition.

As used herein, the term "effective amount" refers to an amount of a biomaterial composition or conjugate or derivative thereof sufficient to exhibit a detectable therapeutic or prophylactic effect without undue adverse side effects (such as toxicity, irritation and allergic response) commensurate with a reasonable benefit/risk ratio when used in the manner of the inventive concept(s). The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Heparosan Synthase (HS) coding sequence yet is isolated away from, or purified free from, unrelated genomic DNA, for example, total *Pasteurella multocida*. Included within the term "DNA segment", are DNA segments and smaller fragments of such segments, and also recombinant vectors, including, for example, plasmids, cosmids, phage, viruses, and the like.

The term "expression" as used herein may include any step involved in the production of heparosan synthases, including but not limited to, transcription and translation.

The terms "gene-optimized" and "gene optimization" as used herein refers to changes in the nucleotide sequence encoding a protein to those preferentially used in a particular host cell such that the encoded protein is more efficiently expressed in the host cell when compared to the native nucleotide sequence. Gene-optimization involves various aspects of improving codon usage and messenger RNA structure to improve protein production. It is well-known in the art that genes from one organism, the source, do not always perform well in a recipient organism. For example, some amino acids (AAs) are encoded by multiple tRNAs (the degenerate code), and each organism has a preferred codon(s) that is used more frequently. If a rare codon is used in a gene, then the ribosome must stall and wait for the rare tRNA to be found before the protein translation can move onto the next amino acid to be added; if the stalling occurs too long, then the ribosome can fall off, and the protein is not made. Similarly, if the mRNA has a secondary structure that interferes with ribosome movement and thus translation, then the ribosome can fall off the messenger RNA, again resulting in less protein production. By studying the DNA sequence of naturally highly produced proteins in the desired host or recipient organism, certain codons for AAs are noted. Therefore, the source gene can be converted to a more highly functional producer if the rare codons are removed, and the more used codons (with respect to the recipient) are used. The protein sequence is the same, but the DNA sequence can differ due to the degenerate tRNA code. As there are many aspects to the translation process, there are multiple important optimization issues that need to be addressed, including but not limited to, codon usage bias, GC content, CpG dinucleotides content, mRNA secondary structure, cryptic splicing sites, premature PolyA sites, internal chi sites and ribosomal binding site, negative CpG islands, RNA instability motifs (ARE), repeat sequences (direct repeat, reverse repeat, and Dyad repeat), addition of Kozak sequences and/or Shine-Dalgarno sequences to increase the efficiency of translational initiation, addition of stop codons to increase the efficiency of translational termination, and the like. Therefore, gene optimization, as used herein, refers to any changes in a nucleotide sequence made to address one or more of the optimization issues mentioned above.

A non-limiting example of a type of gene optimization utilized in accordance with the presently disclosed and/or claimed inventive concept(s) is codon optimization. The terms "codon-optimized" and "codon optimization" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding enzymes may be codon-optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG Codon Preference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066), all of which are expressly incorporated herein by reference. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270), all of which are incorporated herein by reference.

The Dalton (Da) is the international unit of molecular mass based on 1/12 of the mass of carbon 12. A kiloDalton (kDa) is 1,000 Da. A mega-Dalton (MDa) is 1,000 kDa.

Turning now to the presently disclosed and/or claimed inventive concept(s), compositions that include an isolated high molecular weight (HMW) heparosan polymer are included and described in detail herein, along with methods of producing and using same. In certain embodiments, the composition is a biomaterial composition. In particular embodiments, the isolated heparosan polymer is biocompatible with a mammalian patient and biologically inert in extracellular compartments of the mammalian patient. The heparosan polymer is substantially not susceptible to vertebrate (such as but not limited to, mammalian) hyaluronidases or vertebrate (such as but not limited to, mammalian) heparanses and thereby is not substantially degraded in vivo in extracellular compartments of the mammalian patient. In addition, the heparosan polymer may be recombinantly produced as described in detail herein utilizing a combination of host cell and synthase biosynthesis, where features of both of these factors influence the MW made by the live cell.

The disclosed and/or claimed isolated heparosan polymer is represented by the structure (-GlcUA-beta1,4-GlcNAc-alpha-1,4-)n, wherein n is a positive integer greater than or equal to about 2,000. Polymers of this size are hitherto unreported in the scientific literature and prior art. Each single n unit is approximately 400 Da, and therefore the isolated heparosan polymer has a molecular weight (MW) of greater than or equal to about 800 kDa. In particular embodiments, n is a positive integer in a range of from about 2,000 to about 17,000, and therefore the isolated heparosan polymer has a MW in a range of from about 0.8 MDa to about 6.8 MDa. In addition, n may be a positive integer such as but not limited to, 2,250; 2,500; 2,750; 3,000; 3,250; 3,500; 3,750; 4,000; 4,250; 4,500; 4,750; 5,000; 5,250; 5,500; 5,750; 6,000; 6,250; 6,500; 6,750; 7,000; 7,250; 7,500; 7,750; 8,000; 8,250; 8,500; 8,750; 9,000; 9,250; 9,500; 9,750; 10,000; 10,250; 10,500; 10,750; 11,000; 11,250; 11,500; 11,750; 12,000; 12,250; 12,500; 12,750; 13,000; 13,250; 13,500; 13,750; 14,000; 14,250; 14,500; 14,750; 15,000; 15,250; 15,500; 15,750; 16,000; 16,250; 16,500; 16,750; and 17,000; as well as within a range of any of the above.

The heparosan polymer may be linear or cross-linked. The compositions of the presently disclosed and/or claimed inventive concept(s) may be administered to a patient by any means known in the art; for example, but not by way of limitation, the compositions may be injectable and/or implantable. In addition, the compositions may be in a gel or semi-solid state, a suspension of particles, or the compositions may be in a liquid form.

Alternatively, the heparosan polymer may be attached to a substrate. When attached to a substrate, the isolated heparosan polymer may be covalently (via a chemical bond) or non-covalently (via weak bonds) attached to the substrate. Any substrate known in the art or otherwise contemplated herein may be utilized, so long as the substrate is capable of being attached to the heparosan polymer and functioning in accordance with the presently disclosed and/or claimed inventive concept(s). Examples of substrates that may be utilized in accordance with the presently disclosed and/or claimed inventive concept(s) include, but are not limited to, silica, silicon, semiconductors, glass, polymers, nanotubes, nanoparticles, organic compounds, inorganic compounds, metals, and combinations thereof. Non-limiting examples of metals that may be utilized include gold, copper, stainless steel, nickel, aluminum, titanium, thermosensitive alloys, and combinations thereof.

The presently disclosed and/or claimed inventive concept(s) also comprises biomaterial compositions comprising a cross-linked gel that includes an isolated heparosan polymer and at least one cross-linking agent. The cross-linking agent may be any cross-linking agent known or otherwise contemplated in the art; specific non-limiting examples of cross-linking agents that may be utilized in accordance with the presently disclosed and/or claimed inventive concept(s) include aldehydes, epoxides, polyaziridyl compounds, glycidyl ethers, divinyl sulfones, and combinations and derivatives thereof. An advantage of the currently described inventive concept(s) is that lower concentrations of this high MW (greater than 1 MDa or 1,000 kDa) polymer may be used to produce useful gels than if a lower MW polymer was employed.

Any of the biomaterial compositions of the presently disclosed and/or claimed inventive concept(s) may be a moisturizing biomaterial that protects from dehydration; alternatively, any of the biomaterial compositions of the presently disclosed and/or claimed inventive concept(s) may be a lubricating biomaterial.

Another aspect of the presently disclosed and/or claimed inventive concept(s) is related to kits for in vivo administration of any of the compositions described herein above or otherwise contemplated herein to a mammalian patient. The kit may also include instructions for administering the composition to the mammalian patient. The kit may optionally also contain one or more other compositions for use in accordance with the methods described herein.

The presently disclosed and/or claimed inventive concept(s) is further directed to a method of recombinantly producing a high MW heparosan polymer. In the method, a recombinant host cell containing a nucleotide sequence encoding a heparosan synthase, the enzyme that polymerizes the monosaccharides from UDP-sugar precursors into heparosan polysaccharide or sugar polymer, is cultured under conditions appropriate for the expression of the heparosan synthase. The heparosan synthase produces the high MW heparosan polymer, which is then isolated.

The isolated high MW heparosan polymer may possess any or all of the characteristics described herein above, and may subsequently be utilized as a biomaterial composition. Thus, the method may further comprise one or more steps to this end, such as but not limited to, crosslinking the isolated heparosan polymer or attaching (either covalently or non-covalently) the isolated heparosan polymer to any of the substrates described or otherwise contemplated herein.

In certain non-limiting embodiments, the host cell is an *E. coli* host cell, and the heparosan synthase is a *Pasteurella* heparosan synthase.

Any heparosan synthase known in the art or otherwise contemplated herein may be utilized in accordance with the presently disclosed and/or claimed inventive concept(s), so long as the heparosan synthase is capable of producing a high MW heparosan polymer in an appropriate host under the appropriate culture conditions. Non-limiting examples of heparosan synthases that may be utilized in accordance with the presently disclosed and/or claimed inventive concept(s) are described in greater detail herein below.

Any host cell known in the art or otherwise contemplated herein may be utilized in accordance with the presently disclosed and/or claimed inventive concept(s), so long as the host cell is capable of being made recombinant with a heparosan synthase gene and producing a high MW heparosan polymer upon expression of the heparosan synthase gene under the appropriate culture conditions. Non-limiting examples of host cells that may be utilized in accordance with the presently disclosed and/or claimed inventive concept(s) are described in greater detail below.

In one embodiment, the presently disclosed and/or claimed inventive concept(s) shows that *Pasteurella* heparosan synthases (or catalyst with sequence similarity or key motifs) will perform the ultra-high MW heparosan biosynthesis operation in an *E. coli* host cell with the proper UDP-sugar and transport infrastructure. Most available *E. coli* strains employed in laboratories as well as most wild-type isolates are therefore not useful without further manipulation. The presently disclosed and/or claimed inventive concept(s) demonstrates that an *E. coli* K5 host (or strains that contain similar infrastructure) is amenable to high MW heparosan polymer production.

In theory, at least simple two models for controlling the size of a polymer are possible: (A) host cell-controlled biosynthesis or (B) synthase-controlled biosynthesis. In the former model, the nature of the supporting apparatus (e.g., UDP-sugar precursors, transporters) defines the final size distribution made by the live cell. In the latter model, the intrinsic properties of the polymerizing catalyst (e.g., elongation rate, processivity) control the polymer size distribution made by the live cell. A third model (C), combinatorial host cell/synthase biosynthesis, is possible where features of both factors influence the MW made by a live cell; this model is also the most complex, unpredictable, and non-obvious to decipher. For the presently disclosed and/or claimed inventive concept(s), models A & B are inconsistent with the observed data; neither the *Escherichia coli* K5 host cell's product size (~50-80 kDa) nor the *Pasteurella* heparosan synthase product size (~100-300 kDa) is similar to the heparosan made in the inventive concept(s) (>800 kDa) and should be considered a non-predictable outcome that has not been reported in the patent or scientific literature to date.

Certain embodiments of the presently disclosed and/or claimed inventive concept(s) also include the use of alternative hosts with the potential for glycosaminoglycan production, including bacteria from both Gram-negative (e.g., *Pseudomonas*, etc.) and Gram-positive classes (e.g., Bacilli, Lactoctococci, etc.), as well as other microbes (fungi, archae, etc). The basic requirements of a recombinant host for use in heparosan production in accordance with the presently disclosed and/or claimed inventive concept(s) include: (a) the glycosyltransferase(s) that produce heparosan, and (b) the UDP-sugar precursors UDP-GlcNAc and UDP-GlcUA. It should be noted that the latter requirement can be met by either native genes or introduced recombinant genes. The required genes can be either episomally and/or chromosomally located.

In certain embodiments, the host cell further comprises at least one gene encoding an enzyme for synthesis of a heparosan sugar precursor (i.e., UDP-GlcNAc or UDP-GlcUA). Non-limiting examples of genes encoding an enzyme for synthesis of a heparosan sugar precursor that may be utilized in accordance with the presently disclosed and/or claimed inventive concept(s) include pyrophosphorylases, transferases, mutases, dehydrogenases, and epimerases.

The ultra-high MW (= or >1 MDa) heparosan polymer is not known in nature and not been shown or reported by others. As well-known in the polymer field, the size distribution affects its physical properties (e.g., viscosity, chain entanglement, solubility). The >1 MDa heparosan described and claimed in the inventive concept(s) is preferred over the naturally occurring heparosan with respect to performance in production of certain biomaterials, such as but not limited to, viscoelastics and hydrogels.

The presently disclosed and/or claimed inventive concept(s) is also related to methods of augmenting tissue in a mammalian patient. In such methods, an effective amount of any of the biomaterial compositions described herein above or otherwise contemplated herein is administered to the mammalian patient. The biomaterial composition may be administered to the patient by any method known in the art, including, but not limited to, injection and/or implantation. When injected, the biomaterial composition may be in a liquid state or a suspension of particles, whereas when implanted, the biomaterial composition may be in a gel or semi-solid state, or may be attached to a substrate.

The presently disclosed and/or claimed inventive concept(s) also relates to methods of repairing voids in tissues of mammals. In the method, any of the biomaterial compositions described herein above or otherwise contemplated herein is administered into the voids. In certain embodiments, the biomaterial composition may be injected and/or implanted into the voids.

The presently disclosed and/or claimed inventive concept(s) also relates to methods of creating voids or viscus in tissues of mammals. In the method, any of the biomaterial compositions described herein above or otherwise contemplated herein are disposed into a tissue or a tissue engineering construct to create the voids or viscus. In certain embodiments, the biomaterial composition may be injected and/or implanted into the tissue/tissue engineering construct to create the voids or viscus.

The presently disclosed and/or claimed inventive concept(s) also relates to methods of reparative surgery or plastic surgery. In the method, any of the biomaterial compositions described herein above or otherwise contemplated herein is administered to a patient and serves as a filling material at the site to which it is administered. In certain embodiments, the biomaterial composition may be injected and/or implanted into the patient.

The presently disclosed and/or claimed inventive concept(s) further relates to methods of dermal augmentation and/or treatment of skin deficiency in a patient. In the method, any of the biomaterial compositions described herein above or otherwise contemplated herein is administered to the patient. In certain embodiments, the biomaterial composition may be injected and/or implanted into the patient. The biomaterial composition is biocompatible, swellable, hydrophilic, and substantially non-toxic, and the biomaterial composition swells upon contact with physiological fluids at the administration/injection/implantation site.

The dermal augmentation method of the presently disclosed and/or claimed inventive concept(s) is especially suitable for the treatment of skin contour deficiencies, which are often caused by various conditions/exposures, including but not limited to, aging, environmental exposure, weight loss, child bearing, injury, surgery, in addition to diseases such as acne and cancer. Non-limiting examples of contour deficiencies that may be treated in accordance with the presently disclosed and/or claimed inventive concept(s) include frown lines, worry lines, wrinkles, crow's feet, marionette lines, stretch marks, and internal and external scars resulted from injury, wound, bite, surgery, or accident.

In addition, the presently disclosed and/or claimed inventive concept(s) also relates to methods of medical or prophylactic treatment of a mammalian patient. In the method, any of the compositions described herein above or otherwise contemplated herein is administered to the mammalian patient in need of such a treatment. In certain embodiments, the composition may be injected and/or implanted into the mammalian patient.

Further, the presently disclosed and/or claimed inventive concept(s) also relates to methods of treatment or prophylaxis of tissue augmentation in a mammalian patient. In the method, a medical or prophylactic composition comprising a polysaccharide gel composition that includes any of the biomaterial compositions described herein above or otherwise contemplated herein is administered to the mammalian patient.

The presently disclosed and/or claimed inventive concept(s) is further related to a delivery system for a substance having biological or pharmacological activity. The system comprising a molecular cage formed of a cross-linked gel of heparosan or a mixed cross-linked gel of heparosan and at least one other hydrophilic polymer copolymerizable therewith. The system further includes a substance having biological or pharmacological activity dispersed therein, wherein the substance is capable of being diffused therefrom in a controlled manner.

The biomaterials of the presently disclosed and/or claimed inventive concept(s) may be utilized in any methods of utilizing biomaterials known or otherwise contemplated in the art. For example but not by way of limitation, the biomaterial compositions of the presently disclosed and/or claimed inventive concept(s) may be utilized in any of the methods of utilizing other known biomaterials that are described in U.S. Pat. No. 4,582,865, issued to Balazs et al. on Apr. 15, 1986; U.S. Pat. No. 4,636,524, issued to Balazs et al. on Jan. 13, 1987; U.S. Pat. No. 4,713,448, issued to Balazs et al. on Dec. 15, 1987; U.S. Pat. No. 5,137,875, issued to Tsununaga et al. on Aug. 11, 1992; U.S. Pat. No. 5,827,937, issued to Ang on Oct. 27, 1998; U.S. Pat. No. 6,436,424, issued to Vogel et al. on Aug. 20, 2002; U.S. Pat. No. 6,685,963, issued to Taupin et al. on Feb. 3, 2004; and U.S. Pat. No. 7,060,287, issued to Hubbard et al. on Jun. 13, 2006. The entire contents of such patents are hereby expressly incorporated herein by reference, and therefore any of the methods described therein, when utilized with the novel biomaterial compositions of the presently disclosed and/or claimed inventive concept(s), also fall within the scope of the presently disclosed and/or claimed inventive concept(s).

Other specific examples of uses for the biomaterial compositions of the presently disclosed and/or claimed inventive concept(s) include, but are not limited to: (a) a persistent lubricating coating on a surface, such as, but not limited to, surgical devices; (b) a long lasting moisturizer; (c) a viscoelastic supplement for joint maladies; and (d) a non-thrombotic, non-occluding blood conduit (such as, but not limited to, a stent or artificial vessel, etc.). In addition, any of the biomaterial compositions of the presently disclosed and/or claimed inventive concept(s) may be utilized in tissue engineering to form a viscus or vessel duct or lumen by using the biomaterial compositions of the presently disclosed and/or claimed inventive concept(s) as a three-dimensional space maker; in this instance, the surrounding cells will not bind to the biomaterial compositions of the presently disclosed and/or claimed inventive concept(s), thereby making such biomaterial compositions well suited for this technology.

In addition, the presently disclosed and/or claimed inventive concept(s) further includes methods of doing business by producing any of the compositions described or otherwise contemplated herein by the methods described herein above and selling and delivering the compositions to a customer or providing such compositions to a patient.

In one embodiment of the presently disclosed and/or claimed inventive concept(s), the compositions of the presently disclosed and/or claimed inventive concept(s) may be produced using recombinant heparosan synthases as described or otherwise known in the art, including but not limited to, the heparosan synthases disclosed in the inventor's prior patents U.S. Pat. No. 7,307,159, issued Dec. 11, 2007; U.S. Pat. No. 7,771,981, issued May 8, 2002; and U.S. Pat. No. 8,088,604, issued Jan. 3, 2012; as well as the heparosan synthases disclosed in the inventor's published patent applications US 2008/0226690, published Sep. 18, 2008; US 2010/0036001, published Feb. 11, 2010; and US 2012/0108802, published May 3, 2012. The entire contents of the above-referenced patents and patent applications, and especially the sequence listings thereof, are expressly incorporated herein by reference as if explicitly disclosed herein.

Non-limiting examples of heparosan synthases that may be utilized in accordance with the presently disclosed and/or claimed inventive concept(s) include: a recombinant heparosan synthase having an amino acid sequence as set forth in at least one of SEQ ID NOS: 2, 4, and 6-8; a recombinant heparosan synthase encoded by the nucleotide sequence of at least one of SEQ ID NOS: 1, 3, 5, and 9-11; a recombinant heparosan synthase encoded by a nucleotide sequence capable of hybridizing to a complement of the nucleotide sequence of at least one of SEQ ID NOS: 1, 3, 5, and 9-11 under hybridization conditions comprising hybridization at a temperature of 68° C. in 5×SSC/5×Denhardt's solution/1.0% SDS, followed with washing in 3×SSC at 42° C.; a recombinant heparosan synthase encoded by a nucleotide sequence capable of hybridizing to a complement of a nucleotide sequence encoding an amino acid sequence as set forth in at least one of SEQ ID NOS: 2, 4, and 6-8 under hybridization conditions comprising hybridization at a temperature of 68° C. in 5×SSC/5×Denhardt's solution/1.0% SDS, followed with washing in 3×SSC at 42° C.; a recombinant heparosan synthase encoded by a nucleotide sequence capable of hybridizing to a complement of the nucleotide sequence of at least one of SEQ ID NOS: 1, 3, 5, and 9-11 under hybridization conditions comprising hybridization at a temperature of 30° C. in 5×SSC, 5×Denhardts reagent, 30% formamide for about 20 hours followed by washing twice in 2×SSC, 0.1% SDS at about 30° C. for about 15 min followed by 0.5×SSC, 0.1% SDS at about 30° C. for about 30 minutes; and a recombinant heparosan synthase encoded by a nucleotide sequence capable of hybridizing to a complement of a nucleotide sequence encoding an amino acid sequence as set forth in of at least one of SEQ ID NOS: 2, 4, and 6-8 under hybridization conditions comprising hybridization at a temperature of 30° C. in 5×SSC, 5×Denhardts reagent, 30% formamide for about 20 hours followed by washing twice in 2×SSC, 0.1% SDS at about 30° C. for about 15 min followed by 0.5×SSC, 0.1% SDS at about 30° C. for about 30 minutes.

Additional non-limiting examples of heparosan synthases that may be utilized in accordance with the presently disclosed and/or claimed inventive concept(s) include: a recombinant heparosan synthase that is at least 60% identical to at least one of SEQ ID NOS: 2, 4, and 6-8; a recombinant heparosan synthase that is at least 70% identical to at least one of SEQ ID NOS: 2, 4, and 6-8; a recombinant heparosan synthase that is at least 80% identical to at least one of SEQ ID NOS: 2, 4, and 6-8; a recombinant heparosan synthase that is at least 85% identical to at least one of SEQ ID NOS: 2, 4, and 6-8; a recombinant heparosan synthase that is at least 90% identical to at least one of SEQ ID NOS: 2, 4, and 6-8; a recombinant heparosan synthase that is at least 95% identical to at least one of SEQ ID NOS: 2, 4, and 6-8; a recombinant heparosan synthase encoded by a nucleotide sequence that is at least 60% identical to at least one of SEQ ID NOS: 1, 3, 5, and 9-11; a recombinant heparosan synthase encoded by a nucleotide sequence that is at least 70% identical to at least one of SEQ ID NOS: 1, 3, 5, and 9-11; a recombinant heparosan synthase encoded by a nucleotide sequence that is at least 80% identical to at least one of SEQ ID NOS: 1, 3, 5, and 9-11; a recombinant heparosan synthase encoded by a nucleotide sequence that is at least 85% identical to at least one of SEQ ID NOS: 1, 3, 5, and 9-11; a recombinant heparosan synthase encoded by a nucleotide sequence that is at least 90% identical to at least one of SEQ ID NOS: 1, 3, 5, and 9-11; and a recombinant heparosan synthase encoded by a nucleotide sequence that is at least 95% identical to at least one of SEQ ID NOS: 1, 3, 5, and 9-11.

The use of truncated heparosan synthase genes to produce any of the compositions described or otherwise contemplated herein also falls within the scope of the presently disclosed and/or claimed inventive concept(s). For instance, the removal of the last 50 residues or the first 77 residues of PmHS1 (SEQ ID NOS: 7 and 8, respectively) does not inactivate its catalytic function (Kane et al., 2006). Those of ordinary skill in the art would appreciate that simple amino acid removal from either end of the heparosan synthase sequence can be accomplished. The truncated versions of the sequence simply have to be checked for activity in order to determine if such a truncated sequence is still capable of producing heparosan.

Similarly, the use of fusion proteins that add other polypeptide segments (to either termini or internally) to the heparosan synthase sequence also falls within the scope of the presently disclosed and/or claimed inventive concept(s). The fusion protein partner (such as but not limited to, maltose-binding protein, thioredoxin, etc.) can increase stability, increase expression levels in the cell, and/or facilitate the purification process, but the catalytic activity for making the heparosan polymer intrinsic to the inventive concept(s) remains the same.

The recombinant heparosan synthase utilized in accordance with the presently disclosed and/or claimed inventive concept(s) also encompass sequences essentially as set forth in SEQ ID NOS: 1-8. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a heparosan polymer in vitro or in vivo. In the above examples, X refers to either SEQ ID NO:1-11 or any additional sequences set forth herein, such as the truncated or mutated versions of pmHS1 that are contained generally in SEQ ID NOS: 7-8.

It is widely recognized that a pair of distinct enzymes with even 30, 50, or 70% identity or similarity at the active site (of functional regions) thereof can possess the same catalytic activity. As most of the protein sequence is a scaffold for the active site, it is not required that all regions of the enzymes be exactly the same between functional enzyme homologs or analogs. In addition, some extra (non-catalytic) sequences may also be present, thus lowering the total protein similarity levels. Thus, functional regions (and not entire sequences) should be the basis for similarity comparisons between two enzymes.

These references and countless others indicate that one of ordinary skill in the art, given a nucleic acid sequence or an amino acid sequence, could make substitutions and changes to the nucleic acid/amino acid sequence without changing its functionality (specific examples of such changes are given hereinafter and are generally set forth in SEQ ID NOS: 7-8). Also, a substituted nucleic acid segment may be highly identical and retain its enzymatic activity with regard to its unadulterated parent, and yet still fail to hybridize thereto. As such, variations of the sequences that fall within the above-defined functional limitations have been disclosed in the applications incorporated by reference. As such, the presently disclosed and/or claimed inventive concept(s) should not be regarded as being solely limited to the use of the specific sequences disclosed and/or incorporated by reference herein. Even further, if smaller regions or sequence motifs contain the active site residues or important functional units, this similarity is also indicative of function. The presently disclosed and/or claimed inventive concept(s) may utilize nucleic acid segments encoding an enzymatically active HS from *P. multocida*—pmHS1 and/or PmHS2. One of ordinary skill in the art would appreciate that substitutions can be made to the pmHS1 or PmHS2 nucleic acid segments listed in SEQ ID NO:1, 3 and 5, respectively, without deviating outside the scope and claims of the presently disclosed and/or claimed inventive concept(s). Standardized and accepted functionally equivalent amino acid substitutions are presented in Table 1. In addition, other analogous or homologous enzymes that are functionally equivalent to the disclosed synthase sequences would also be appreciated by those skilled in the art to be similarly useful in the methods of the presently disclosed and/or claimed inventive concept(s), that is, a new method to control precisely the size distribution of the heparosan polymer.

TABLE 1

| Amino Acid Group | Conservative and Semi-Conservative Substitutions |
| --- | --- |
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Therefore, the presently disclosed and/or claimed inventive concept(s) also includes the use of heparosan synthases that have amino acid sequences that differ from at least one of SEQ ID NOS: 2, 4, and 6-8 by at least one of the following: the presence of 1-60 amino acid additions, deletions, or substitutions when compared to at least one of SEQ ID NOS: 2, 4, and 6-8; the presence of 1-55 amino acid additions, deletions, or substitutions when compared to at least one of SEQ ID NOS: 2, 4, and 6-8; the presence of 1-50 amino acid additions, deletions, or substitutions when compared to at least one of SEQ ID NOS: 2, 4, and 6-8; the presence of 1-45 amino acid additions, deletions, or substitutions when compared to at least one of SEQ ID NOS: 2, 4, and 6-8; the presence of 1-40 amino acid additions, deletions, or substitutions when compared to at least one of SEQ ID NOS: 2, 4, and 6-8; the presence of 1-35 amino acid additions, deletions, or substitutions when compared to at least one of SEQ ID NOS: 2, 4, and 6-8; the presence of 1-30 amino acid additions, deletions, or substitutions when compared to at least one of SEQ ID NOS: 2, 4, and 6-8; the presence of 1-25 amino acid additions, deletions, or substitutions when compared to at least one of SEQ ID NOS: 2, 4, and 6-8; the presence of 1-20 amino acid additions, deletions, or substitutions when compared to at least one of SEQ ID NOS: 2, 4, and 6-8; the presence of 1-15 amino acid additions, deletions, or substitutions when compared to at least one of SEQ ID NOS: 2, 4, and 6-8; the presence of 1-10 amino acid additions, deletions, or substitutions when compared to at least one of SEQ ID NOS: 2, 4, and 6-8; and the presence of 1-5 amino acid additions, deletions, or substitutions when compared to at least one of SEQ ID NOS: 2, 4, and 6-8.

Allowing for the degeneracy of the genetic code as well as conserved and semi-conserved substitutions, sequences which have between about 40% and about 99%; or more preferably, between about 60% and about 99%; or more preferably, between about 70% and about 99%; or more preferably, between about 80% and about 99%; or even more preferably, between about 90% and about 99% identity to the nucleotides of at least one of SEQ ID NO: 1, 3, 5, and 9-11 will be sequences which are "essentially as set forth in at least one of SEQ ID NO: 1, 3, 5 and 9-11. Sequences which are essentially the same as those set forth in at least one of SEQ ID NO: 1, 3, 5 and 9-11 may also be functionally defined as sequences which are capable of hybridizing to a nucleic acid segment containing the complement of at least one of SEQ ID NO: 1, 3, 5, and 9-11 under standard stringent hybridization conditions, "moderately stringent hybridization conditions," "less stringent hybridization conditions," or "low stringency hybridization conditions." Suitable standard or less stringent hybridization conditions will be well known to those of skill in the art and are clearly set forth hereinbelow. In a preferred embodiment, standard stringent hybridization conditions or less stringent hybridization conditions are utilized.

The terms "standard stringent hybridization conditions," "moderately stringent conditions," and less stringent hybridization conditions or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a heparin/heparosan synthase or its complement, such as SEQ ID NO:1, 3, 5, 9, 10, or 11, or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., Standard Saline Citrate (SSC), Saline Sodium Phosphate EDTA (SSPE), or High Phosphate Buffer (HPB) solutions). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by about 5° C.). In practice, the change in $T_m$ can be between about 0.5° C. and about 1.5° C. per 1% mismatch. Examples of standard stringent hybridization conditions include hybridizing at about 68° C. in 5×SSC/5×Denhardt's solution/1.0% SDS, followed with washing in 0.2×SSC/0.1% SDS at room temperature or hybridizing in 1.8×HPB at about 30° C. to about 45° C. followed by washing a 0.2-0.5×HPB at about 45° C. Moderately stringent conditions include hybridizing as described above in 5×SSC\5×Denhardt's solution 1% SDS washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5×Denhardts reagent, 30% formamide at about 30° C. for about 20 hours followed by washing twice in 2×SSC, 0.1% SDS at about 30° C. for about 15 min followed by 0.5×SSC, 0.1% SDS at about 30° C. for about 30 min (FEMS Microbiology Letters, 2000, vol. 193, p. 99-103); (B) hybridizing in 5×SSC at about 45° C. overnight followed by washing with 2×SSC, then by 0.7×SSC at about 55° C. (J. Viological Methods, 1990, vol. 30, p. 141-150); or (C) hybridizing in 1.8×HPB at about 30° C. to about 45° C.; followed by washing in 1×HPB at 23° C.

The DNA segments that may be utilized to produce the compositions of the presently disclosed and/or claimed inventive concept(s) encompass DNA segments encoding biologically functional equivalent HS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HS protein or to test HS mutants in order to examine HS activity at the molecular level or to produce HS mutants having changed or novel enzymatic activity and/or sugar substrate specificity.

The presently disclosed and/or claimed inventive concept(s) also include the use of nucleotide sequences encoding any of the heparosan synthases described or otherwise contemplated herein, wherein the nucleotide sequences are synthetic sequences that have been gene-optimized for expression in a particular host cell. Specific, non-limiting examples of gene-optimized heparosan synthase encoding nucleotide sequences are provided in SEQ ID NOS: 9-11. SEQ ID NOS: 9-10 include nucleotide sequences encoding the heparosan synthase of SEQ ID NO:2 and which have been gene-optimized for expression in *E. coli*. SEQ ID NO:11 includes a nucleotide sequence encoding the heparosan synthase of SEQ ID NO:2 and which have been gene-optimized for expression in *Bacillus*.

However, the scope of the inventive concept(s) is not limited to these particular sequences, but rather includes gene-optimized nucleotide sequences that encode any heparosan synthase described or otherwise contemplated herein (such as, but not limited to heparosan synthase amino acid sequences that are a certain percentage identical to at least one of SEQ ID NOS: 2, 4, and 6-8, as well as heparosan synthase amino acid sequences that contain one or more additions, deletions, or substitutions when compared to at least one of SEQ ID NOS: 2, 4, and 6-8).

The use of gene-optimized sequences is known and used in the art to increase expression of the gene sequence within the heterologous host. However, a novel product was unexpectedly produced from the heparosan synthase expressed in *E. coli* when the *Pasteurella* gene sequence was gene-optimized and expressed in *E. coli*. The inventive concept(s) disclose the production of mega-Dalton molecular weight heparosan polymers, and this novel species has never before been reported in any known microbes. One of ordinary skill in the art would assume that optimization of a gene sequence encoding an enzyme would result in increased expression of that enzyme in the heterologous host, thereby resulting in increased production of the same enzyme-derived product (i.e., higher amounts of the heparosan polymer of the typical size found in the native microbes) produced in the native host. Unexpectedly, the expression of gene-optimized *Pasteurella multocida* heparosan synthase in *E. coli* resulted in a new species of product—an ultra-high molecular weight heparosan polymer. Production of heparosan polymers of this size have not been reported for any other microbe. In addition, the heparosan polymers produced in accordance with the presently disclosed and/or claimed inventive concept(s) exhibit superior and advantageous properties compared to the lower molecular weight products currently known in the art. These properties provide enhanced utility for the heparosan polymer in the biomaterials field. For example but not by way of limitation, the ultra-high molecular weight (MW) heparosan polymers produced in accordance with the presently disclosed and/or claimed inventive concept(s) exhibit enhanced solution viscosity and can be used at lower concentrations (either with or without chemical crosslinking) than the naturally occurring heparosan preparations.

The presently disclosed and/or claimed inventive concept(s) further includes isolated nucleotide sequences, along with recombinant host cells containing same, that contain any of the gene-optimized heparosan synthase sequences disclosed or otherwise contemplated herein.

Heparosan, a sugar polymer that is the natural biosynthetic precursor of heparin and heparan sulfate, has numerous characteristics that indicate that this material exhibits enhanced performance in a variety of medical applications or medical devices. In comparison to HA and heparin, two very structurally similar polymers used in many current applications in several large markets, heparosan is more stable in the body, as no naturally occurring enzymes degrade heparosan, and therefore the biomaterial compositions of the presently disclosed and/or claimed inventive concept(s) should have longer lifetimes compared to presently used biomaterials. In addition, heparosan interacts with fewer proteins (thus less fouling) and cells (thus less infiltration, scarring, or clotting) when compared to existing biomaterials.

The heparosan chain does not contain sulfate groups; thus, the degrading enzyme heparanase, the anticoagulation system proteins of blood, the cell surface binding receptors, and growth factors and cytokines will not specifically bind the polymer. This characteristic leads to an inert character in the body, thereby providing long half-life in the extracellular space in addition to not stimulating or inducing cellular behaviors (e.g., growth, migration, binding, activation, etc). However, once in the cell, the heparosan chain can be degraded by normal metabolic systems such as the exoglycosidases in the lysososme.

In comparison to synthetic plastics or carbon, the natural hydrophilicity (aka water-loving) characteristics of heparosan also enhance tissue compatibility. Animal-derived proteins (e.g., collagen, bovine serum albumin) and calcium hydroxyapatite often have side effects, including but not limited to, eliciting an allergic response and/or stimulating granulation (5). On the other hand, even certain pathogenic bacteria use heparosan to hide in the body since this polymer is non-immunogenic (8-10). The biomaterial compositions of the presently disclosed and/or claimed inventive concept(s) produced from a non-animal source also promise to be free of adventitious agents (e.g., vertebrate viruses, prions) that could potentially contaminate animal- or human-derived sources.

Certain carbohydrates play roles in forming and maintaining the structures of multicellular organisms in addition to more familiar roles as nutrients for energy. Glycosaminoglycans [GAGS], long linear polysaccharides consisting of disaccharide repeats that contain an amino sugar, are well-known to be essential in vertebrates (9, 11-15). The GAG structures possess many negative groups and are replete with hydroxyl groups; therefore these sugars have a high capacity to adsorb water and ions. Heparin/heparan (backbone

[β4GlcUA-α4GlcNAc]$_n$), chondroitin (backbone [β4GlcUA-β3GalNAc]$_n$), and hyaluronan (HA; backbone [β4GlcUA-β3GlcNAc]$_n$) are the three most prevalent GAGs in humans. Depending on the tissue and cell type, the GAGs are structural, adhesion, and/or signaling elements. A few clever microbes also produce extracellular polysaccharide coatings, called capsules, composed of GAG chains that serve as virulence factors (9, 10). The capsule is thought to assist in the evasion of host defenses such as phagocytosis and complement. As the microbial polysaccharide is identical or very similar to the host GAG, the antibody response is either very limited or non-existent.

In humans, heparosan only exists transiently, serving as a precursor to the more highly modified final products of heparan sulfate and heparin. In contrast, the bacterial strains set forth herein produce heparosan as their final product (16). Due to the less complex makeup of bacterial cells and to the relative ease with which their growth and expression can be modulated, harvesting a polymer from microbes is much easier, more scalable, and less expensive than extracting from animal tissues. In addition, the polymer in the currently described inventive concept(s), namely the ultra high MW (1 to 6.8 MDa) heparosan derived from our recombinant system has not previously existed or been reported in nature.

Dermal fillers serve as soft tissue replacements or augmentation agents (5, 6). The need for a dermal filler may arise from aging (loss of HA and elastin), trauma (loss of tissue), acne (severe pitting), and/or atrophy (certain wasting diseases including lipoatrophy). Three important characteristics that dermal fillers must possess include a) space-filling ability, b) maintenance of hydration, and c) biocompatibility (5). Currently, polysaccharides, proteins, plastics, and ceramics have been used as biomaterials in dermal fillers. With respect to aesthetic appearance and ease of implantation, softer injectable gels have better attributes; thus, polysaccharides and proteins are widely used. In addition to therapeutic uses, cosmetic applications are becoming more widespread. Alternatives to dermal filler treatment are the use of (i) plastic surgery (tightening the skin), (ii) nerve killing agents such as BOTOX® (relax muscles), and (iii) the use of autologous fat. Compared to dermal fillers, these alternatives are more invasive and/or leave the patient with an unnatural appearance (5, 6). For victims of trauma, scarring, or severe disease, an aim of the therapy is to instill more self-confidence and better disposition; this effect should not be discounted, as a patient's state of mind is important for overall healing.

A major goal of bioengineering is the design of implanted artificial devices to repair or to monitor the human body. High-strength polymers, durable alloys, and versatile semiconductors have many properties that make these materials desirable for bioengineering tasks. However, the human body has a wide range of defenses and responses that evolved to prevent infections and to remove foreign matter that hinders the utilization of modern man-made substances (17, 18). Improving the biocompatibility of these materials will remove a significant bottleneck in the advancement of bioengineering.

A leading example of a medical need for improved surface coatings lies in cardiovascular disease. Damage from this disease is a very prevalent and expensive problem; the patient's system is oxygen- and nutrient-starved due to poor blood flow. The availability of blood vessel grafts from transplants (either autologous or donor) is limited as well as expensive. Therefore, the ability to craft new artificial vessels is a goal, but will take more time to perfect due to the complex engineering and biological requirements. Another current, more approachable therapeutic intervention employs stents, artificial devices that prop open the inner cavity of a patient's blood vessel. As summated by Jordan & Chaikof, "The development of a clinically durable small-diameter vascular graft as well as permanently implantable biosensors and artificial organ systems that interface with blood, including the artificial heart, kidney, liver, and lung, remain limited by surface-induced thrombotic responses" (7). Thus, to advance this technology further, thromboresistant surface coatings are needed that inhibit: (i) protein and cell adsorption, (ii) thrombin and fibrin formation, and (iii) platelet activation and aggregation.

Artificial plastics (poly[lactide] in SCULPTRA® (Sanofi-Aventis) or poly[methylmethacrylate] in ARTECOLL® (Artes Medical, Inc., San Diego, Calif.), ceramics (calcium hydroxyapatite in RADIESSE® (Bioform Medical, Inc., San Mateo, Calif.)) or pure carbon have utility for many therapeutic applications (1,5,7,18), but in many respects, their chemical and physical properties are not as optimal as polysaccharides for the targeted goals of dermal fillers or surface coatings. The most critical issues are lack of good wettability (due to poor interaction with water) and/or hardness (leading to an unnatural feel or brittleness). The presently disclosed and/or claimed inventive concept(s) is related to the use of heparosan to replace and supplant useful sugar polymers that are hydrophilic (water loving) and may be prepared in a soft form.

In addition to HA and heparin, other polysaccharides such as dextran ([α6Glc]$_n$), cellulose ([β4Glc]$_n$), or chitosan ([β4GlcN]$_n$) have many useful properties, but since they are not naturally anionic (negatively charged), these polymers do not mimic the natural extracellular matrix or blood vessel surfaces. Cellulose and dextran can be chemically transformed into charged polymers that help increase their biocompatibility and improve their general physicochemical properties, but harsh conditions are required leading to batch-to-batch variability and quality issues. On the other hand, GAGs, the natural polymers, have intrinsic negative charges.

HA and heparin have been employed as biomaterial coatings for vascular prosthesis and stents (artificial blood vessels and supports), as well as coatings on intraocular lenses and soft-tissue prostheses (7, 22). The rationale is to prevent blood clotting, enhance fouling resistance, and prevent post-surgery adhesion (when organs stick together in an undesirable fashion). The biomaterial compositions of the presently disclosed and/or claimed inventive concept(s) should also be suitable as a coating, as described in greater detail herein after.

A key advantage with heparosan is that it has increased biostability in the extracellular matrix when compared to other GAGs. As with most compounds synthesized in the body, new molecules are made, and after serving their purpose, are broken down into smaller constituents for recycling. Heparin and heparan sulfate are eventually degraded and turned over by a single enzyme known as heparanase (23, 24). Experimental challenge of heparosan and N-sulfo-heparosan with heparanase, however, shows that these polymers lacking 0-sulfation are not sensitive to enzyme action in vitro (25, 26). These findings demonstrate that heparosan is not fragmented enzymatically in the body. Overall, this indicates that heparosan is a very stable biomaterial.

EXAMPLES

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

Gene-optimized pmHS1 sequences for expression in *E. coli* and *Bacillus*. Three gene-optimized sequences encoding the *Pasteurella multocida* heparosan synthase of SEQ ID NO:2 were obtained. Two of the sequences (SEQ ID NOS: 9 and 10) were gene-optimized for expression in *E. coli*, while the third sequence (SEQ ID NO:11) was gene-optimized for expression in *Bacillus*.

Figure 1B:
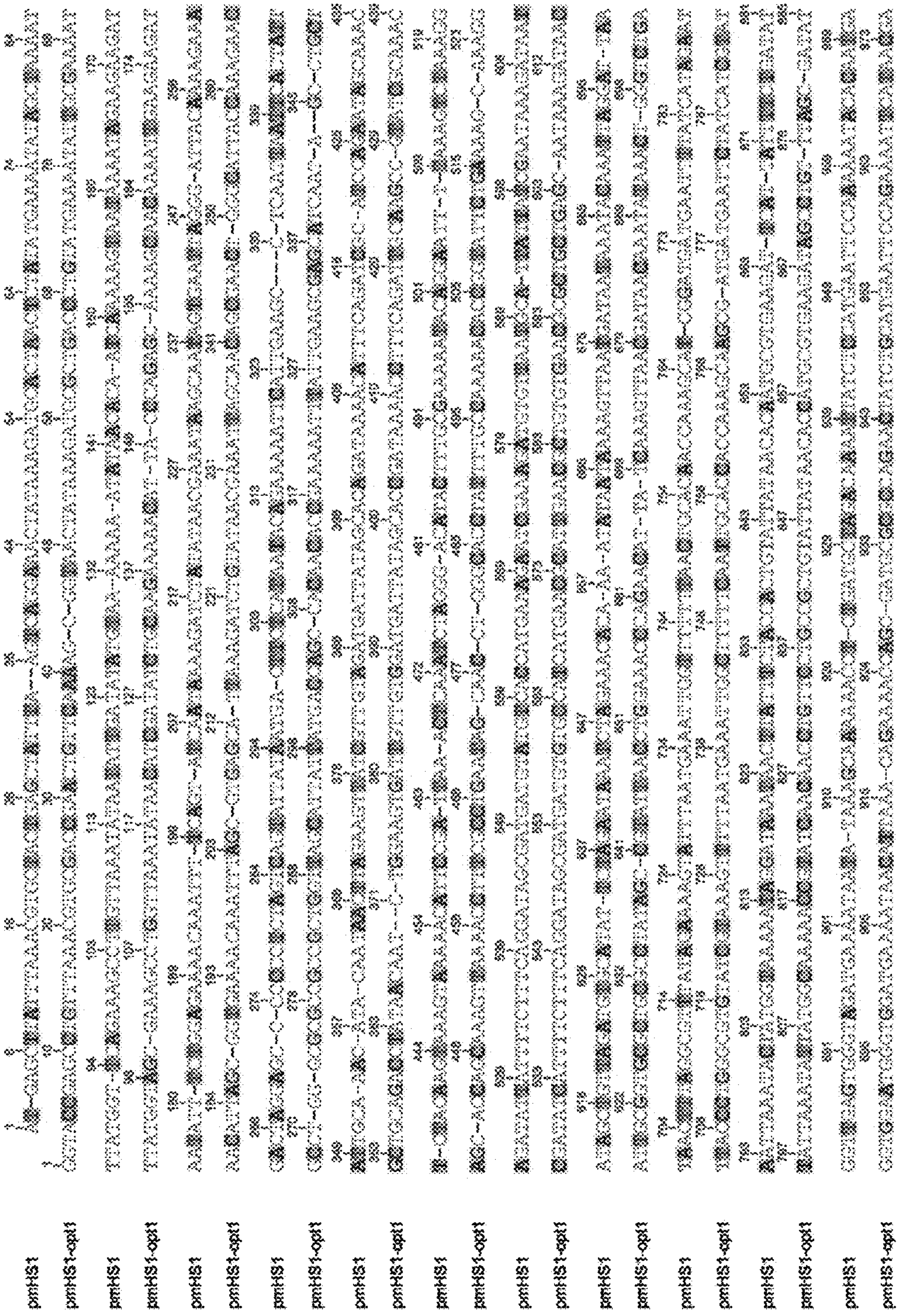
FIG. 1B contains an alignment of the two *E. coli* gene-optimized sequences (SEQ ID NOS: 9 and 10).
Figure 1B:
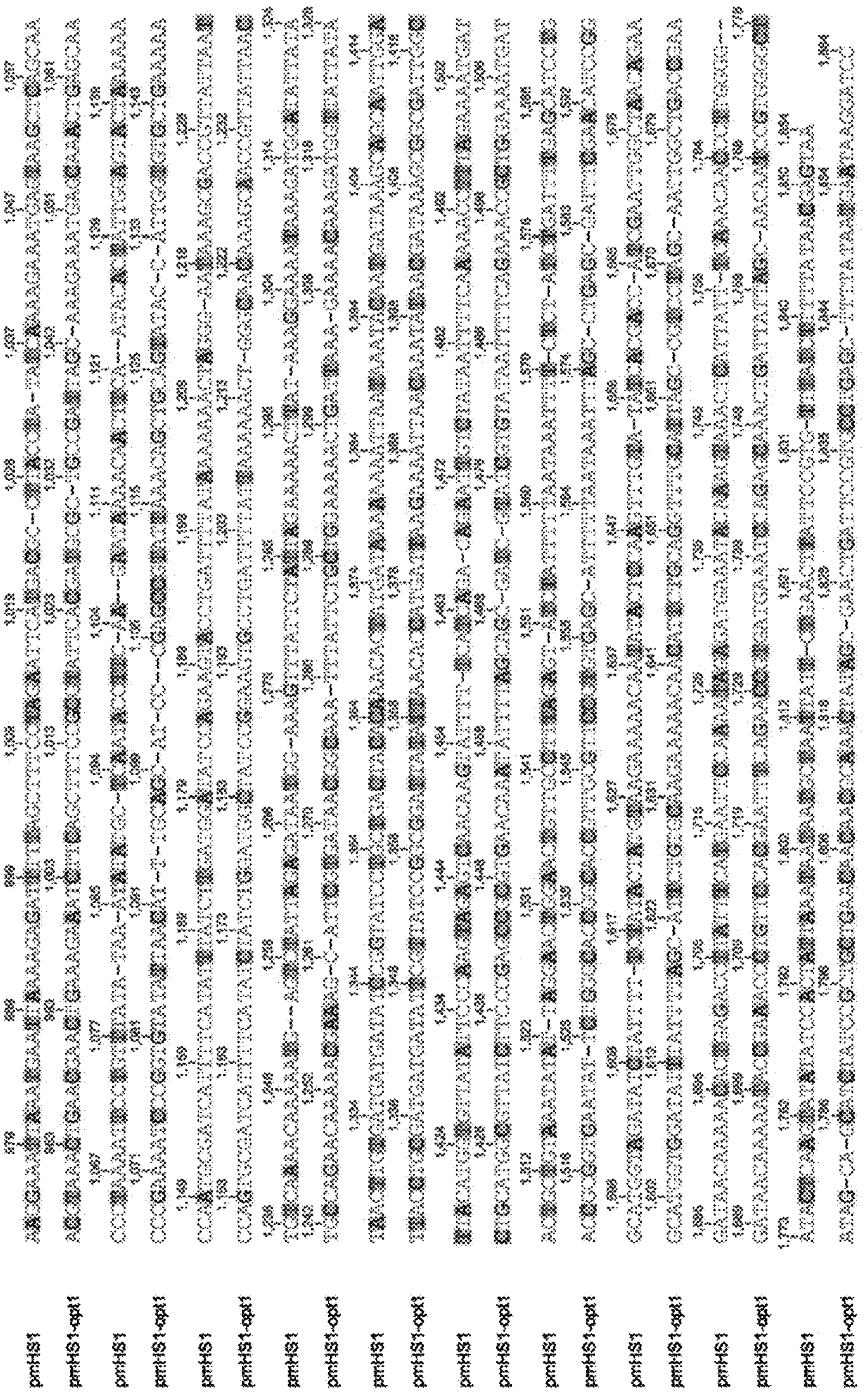

FIG. 1A contains an alignment of the two *E. coli* gene-optimized sequences, SEQ ID NOS: 9 and 10, with the native *Pasteurella multocida* heparosan synthase gene (SEQ ID NO:1). FIG. 1B contains an alignment of only the two *E. coli* gene-optimized sequences, SEQ ID NOS: 9 and 10. FIG. 1C contains an alignment of the *Bacillus* gene-optimized sequence (SEQ ID NO:11) with the native *Pasteurella multocida* heparosan synthase gene (SEQ ID NO:1).

Table 2 illustrates the percent identity between the two gene-optimized sequences of SEQ ID NOS: 9-10 and the native *Pasteurella multocida* gene sequence (SEQ ID NO:1). Note that all three sequences encode amino acid sequences that are 100% identical to the amino acid sequence of SEQ ID NO:2. As can be seen, the two gene-optimized sequences are approximately 74% identical to the native *Pasteurella* gene sequence. It is also noted that the two gene-optimized sequences are only 95% identical to each other, so there is some variation obtained from the algorithm that is being used to generate the optimized sequence.

TABLE 2

Percent Identities of Gene-optimized and Native Heparosan Synthase Gene Sequences

| | pmHS1 (SEQ ID NO: 1) | pmHS1-opt1 (SEQ ID NO: 9) | pmHS1-opt2 (SEQ ID NO: 10) |
|---|---|---|---|
| pmHS1 (SEQ ID NO: 1) | | 74.3% | 73.7% |
| pmHS1-opt1 (SEQ ID NO: 9) | 74.3% | | 94.5% |
| pmHS1-opt2 (SEQ ID NO: 10) | 73.7% | 94.5% | |

Example 2

Production of High MW Heparosan Polysaccharide.

There are two types of naturally occurring micobes, (a) certain *Pasteurella multocida* bacteria (Type D) and their related brethren such as certain Avibacteria, and (b) *Escherichia coli* K5 and their related brethren that make an extracellular coating composed of unsulfated heparosan polymer that is readily harvested from the culture media. An unexpected and advantageous characteristic has been discovered for the recombinant (gene-optimized *Pasteurella* gene in an *E. coli* host) heparosan over both natural bacterial heparosan and mammalian heparin; the heparosan produced in accordance with the presently disclosed and/or claimed inventive concept(s) has a higher molecular weight of approximately 1 to 6.8 MDa (1,000 to 6,800 kDa); therefore, gels or liquid viscoelastics formed of this recombinant heparosan should be easier to produce.

Transformation of Gene-Optimized PmHS1 into *E. coli:*

Synthetic pmHS1 gene-optimized nucleotide sequence (SEQ ID NO:9) was obtained from GenScript USA Inc. (Piscataway, N.J.) and ligated into a pKK223-3 plasmid. The plasmid containing the pmHS1 gene was then transformed into chemically competent *E. coli* K5 cells.

Heparosan Production and Testing:

*E. coli* K5 cells expressing the gene-optimized pmHS1 gene were grown in synthetic media at 30° C. in a 14 L fermentor for approximately 40 hours. Spent culture medium (the liquid part of culture after microbial cells are removed) was harvested (by centrifugation at 10,000×g for 60 minutes), and aliquots thereof were analyzed by agarose gel electrophorsis (1×TAE buffer, 0.8-1.5% agarose) followed by visualization with Stains-All (Lee & Cowman, Anal. Biochem., 1994). The heparosan polymer size was determined by comparison to monodisperse HA size standards (HiLadder, Hyalose, LLC).

The yield of the heparosan in the spent media was checked by carbazole assays for uronic acid. The carbazole assay is a spectrophotometric chemical assay that measures the amount of uronic acid in the sample via production of a pink color; every other sugar in the heparosan chain is a glucuronic acid. The detection limit of the carbazole assay is approximately 5 micrograms of polymer.

The identity of the polymer as heparosan was tested by heparin lyase III (Pedobacter) digestion; any heparin-like polysaccharide will be cleaved into small fragments (oligosaccharides) that run at the dye front on an agarose gel and do not stain well with Stains-All.

Various advantages of the presently disclosed and/or claimed inventive concept(s) are outlined in Tables 3 and 4.

TABLE 3

Comparison of Heparosan and Existing Surgical Biomaterials for Coating Applications

| Key Variable | Project Target | Current Practice | Associated Barrier of Current Procedure | Innovative Approaches Disclosed Herein |
|---|---|---|---|---|
| Coating Stability | Long lasting (weeks-months) | HA, heparin, Bovine serum albumin (BSA) | Degraded by body's natural enzymes | Use heparosan, a polymer that is not enzymatically digested in human body |
| | | Carbon (C) | — | |
| | | Lipids (L) | Shed from surface | |

TABLE 3-continued

Comparison of Heparosan and Existing Surgical Biomaterials for Coating Applications

| Key Variable | Project Target | Current Practice | Associated Barrier of Current Procedure | Innovative Approaches Disclosed Herein |
|---|---|---|---|---|
| Wettability | Freely interacts with water | BSA, HA, heparin, L<br>C | —<br>Hydrophobic | Use water-loving heparosan polymer |
| Fouling, Clotting | Surface does not bind proteins or cells | HA, heparin<br>BSA, C, L | Blood cells & clotting factors bind<br>— | Use relatively biologically inert heparosan polymer |
| Disease Transmission | Zero risk of animal virus or prions | HA [chicken], CG<br>HA [bacterial], PP, CHP | Potential risk<br>— | Use non-animal, bacterially derived heparosan |

TABLE 4

Comparison of Heparosan and Existing Biomaterials for Surface Coating Applications

| Key Variable | Project Target | Current Practice | Associated Barrier of Current Procedure | Innovative Approaches Disclosed Herein |
|---|---|---|---|---|
| Semi-stable Gel Formation | Injectable, Soft, long-lasting (>12-24 months), but not permanent gel | Hyaluronan Gel (HA)<br>Collagen Gel (CG)<br>Plastic Particles (PP)<br>Ca Hydroxyapatite Particles (CHP) | Too short lifetime<br>Grainy appearance & too long lifetime<br>Grainy appearance too long lifetime, & cannot inject easily | Use heparosan, a polymer that is not enzymatically digested in human body, and is not a coarse, hard material |
| Immunogenicity, Allergenicity | No antibody generation | HA [bacterial], PP, CHP<br>HA [chicken], CG [bovine >human] | —<br>Immune or allergic response | Use heparosan polymer that looks 'human' and does not trigger immune system |
| Infiltration | Reduce cell adhesion and/or signaling | HA<br>PP, CHP<br>CG | Proteins & cells bind<br>—<br>Cells bind | Use heparosan polymer that lacks known adhesion domains or chemotactic signals |
| Disease Transmission | Zero risk of human or animal virus and/or prions | HA [chicken], CG<br>HA [bacterial], PP, CHP | Potential risk<br>— | Use non-animal, bacterially derived heparosan |
| X-ray Imaging Compatible | No opaque or marked areas | HA, CG<br>PP, CHP | —<br>Obscures images | Use X-ray-transparent heparosan |
| Abundant Resource | Renewable & not overly expensive to produce | CG [human]<br>HA, CHP, PP, CHP | Limited tissue bank supply or cell culture derived (costly)<br>— | Use heparosan made via bacterial fermentation |

Example 3

Production of Mega-Dalton Molecular Weight Heparosan.

Figure 2:
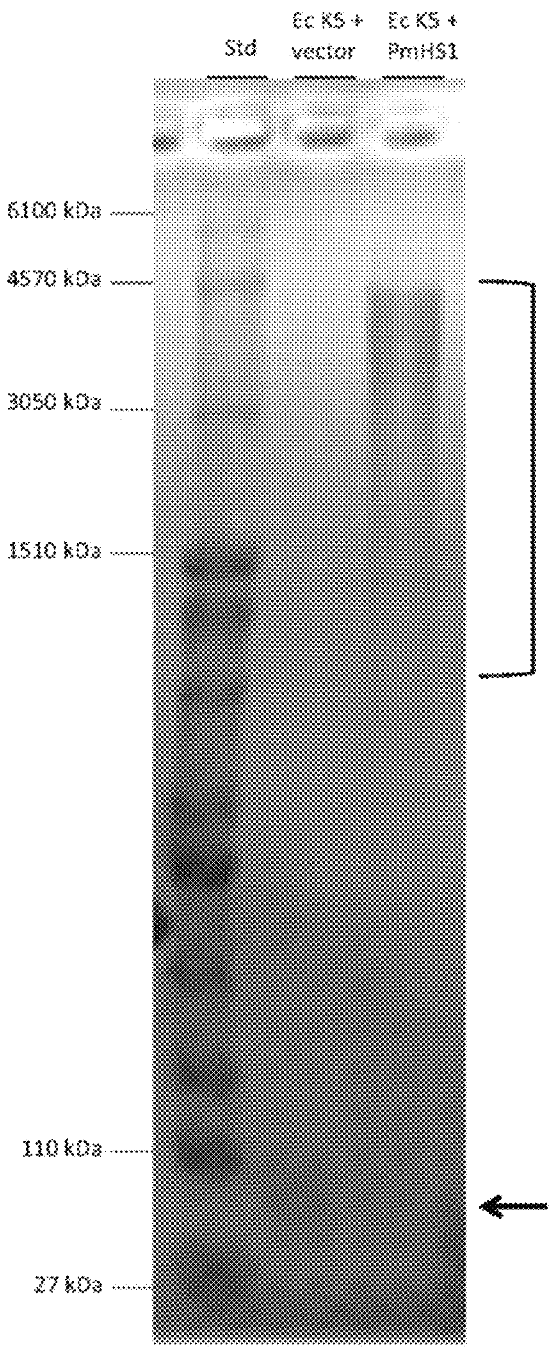
FIG. 2 depicts a gel analysis demonstrating the production of ultra-high molecular weight heparosan polymer in *E. coli* K5 with plasmid-borne recombinant PmHS1 gene from *P. multocida* Type D.

Agarose gel analysis of ultra-high molecular weight heparosan polymer produced according to the method of Example 2 was performed. The agarose gel analysis (1×TAE, Stains-All detection) shown in FIG. 2 demonstrated that the construct of the plasmid-borne recombinant PmHS1 gene from *P. multocida* Type D in *E. coli* K5 (Ec K5+pmHS1) produced a very high MW heparosan polymer (~1 to ~4.5 MDa; band marked with a bracket). As a negative control, the same *E. coli* host with vector alone (Ec K5+vector) only produced a low MW polymer (~50 kDa to ~100 kDa; marked with an arrow). Std=SelectHA Mega-Ladder/SelectHA HiLadder/Select HA LoLadder (Hyalose LLC) with bands from top to bottom: 6100, 4570, 3050, 1510, 1090, 966, 572, 495, 310, 214, 110, 27 kDa (kDa=1,000 Da; MDa=1,000 kDa). Plasmids: Vector=(pKK223-3); PmHS1=(pKK223-3/PmHS1).

Example 4

Production of Mega-Dalton Molecular Weight Heparosan in *E. coli* BL21(DE3).

Figure 3:
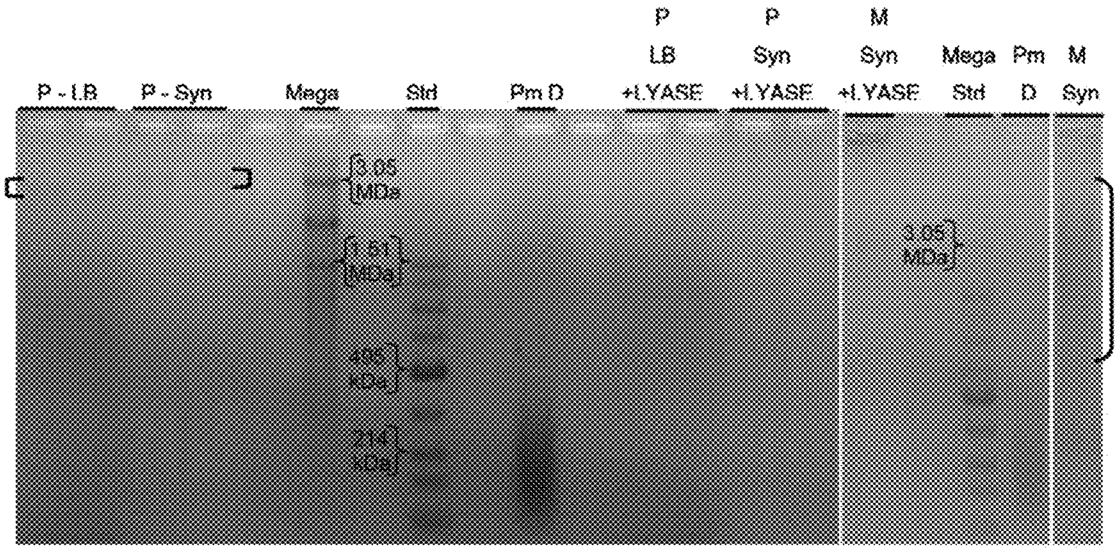
FIG. 3 depicts a gel analysis demonstrating the production of ultra-high molecular weight heparosan polymer in *E. coli* BL21(DE3) with either plasmid-borne recombinant PmHS1 gene or an expression plasmid that produces a maltose-binding protein (MBP) PmHS1 fusion protein.

*E. coli* BL21(DE3) [NEB], an *E. coli* strain with distinct genetics from K5 and K12 strains, was transformed with either pKK223-3/gene-optimized PmHS1 (P) or pMAL-C4e/gene-optimized PmHS1 (M), an expression plasmid producing a maltose-binding protein (MBP)-PmHS1 fusion protein. Cultures of the transformants were induced with IPTG and then grown overnight in either LB (LB) or a synthetic media (Syn). The culture media was then clarified by centrifugation and the heparosan polymer concentrated by ethanol precipitation. The identity of the heparosan polymer was confirmed by digestion with heparin lyase III (+LYASE). The agarose gel analysis (1×TAE, Stains-All detection) shown in FIG. 3 demonstrated that the construct of the plasmid-borne recombinant PmHS1 gene from *P. multocida* Type D in *E. coli* BL21(DE3) produced a very high MW heparosan polymer (~2 to 6.8 MDa; extent of the high MW band marked with a bracket). Mega=SelectHA MegaLadder (Hyalose LLC) with bands from top to bottom: 6100, 4570, 3050, 1510 kDa, Std=SelectHA HiLadder/SelectHA LoLadder (Hyalose LLC) with bands from top to bottom: 1510, 1090, 966, 572, 495, 310, 214, 110, 27 kDa (kDa=1,000 Da; MDa=1,000 kDa).

Example 5

Production of Mega-Dalton Molecular Weight Heparosan in *E. coli* BL21 Express $I^q$.

Figure 4:
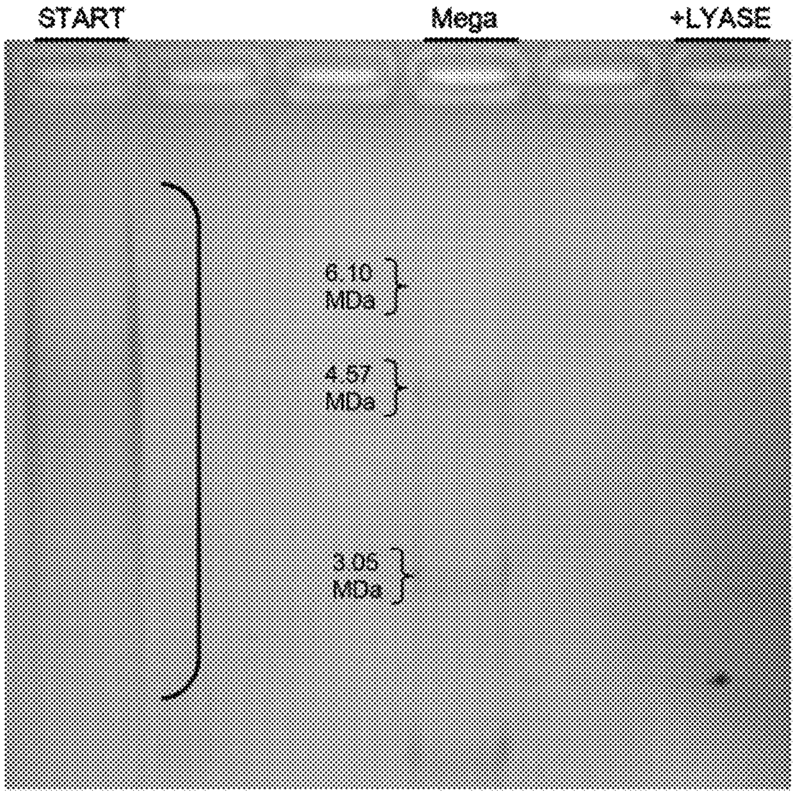
FIG. 4 depicts a gel analysis demonstrating the production of ultra-high molecular weight heparosan polymer in *E. coli* BL21Express $I^q$ transformed with the expression plasmid that produces the maltose-binding protein (MBP) PmHS1 fusion protein.

*E. coli* BL21Express $I^q$ (NEB) was transformed with pMAL-C4e/gene-optimized PmHS1, an expression plasmid producing an MBP-PmHS1 fusion protein. Cultures of the transformants were induced with IPTG and then grown overnight in synthetic media. The culture media was then clarified by centrifugation, and the heparosan polymer concentrated by ethanol precipitation. The identity of the heparosan polymer was confirmed by digestion of the polymer (START) with heparin lyase III (+LYASE). The agarose gel analysis (1×TAE, Stains-All detection) shown in FIG. 4 demonstrated that the construct of the plasmid-borne recombinant, gene-optimized PmHS1 gene (encoding PmHS from *P. multocida* Type D) in *E. coli* BL21 Express $I^q$ produced a very high MW heparosan polymer (~2 to 6.8 MDa; band marked with a bracket). Mega=SelectHA MegaLadder (Hyalose LLC) with bands from top to bottom: 6100, 4570, 3050, 1510 kDa.

Example 6

Effect of Deletion of Heparosan Production in *E. coli* K5 on Production of Mega-Dalton Molecular Weight Heparosan.

Figure 5:
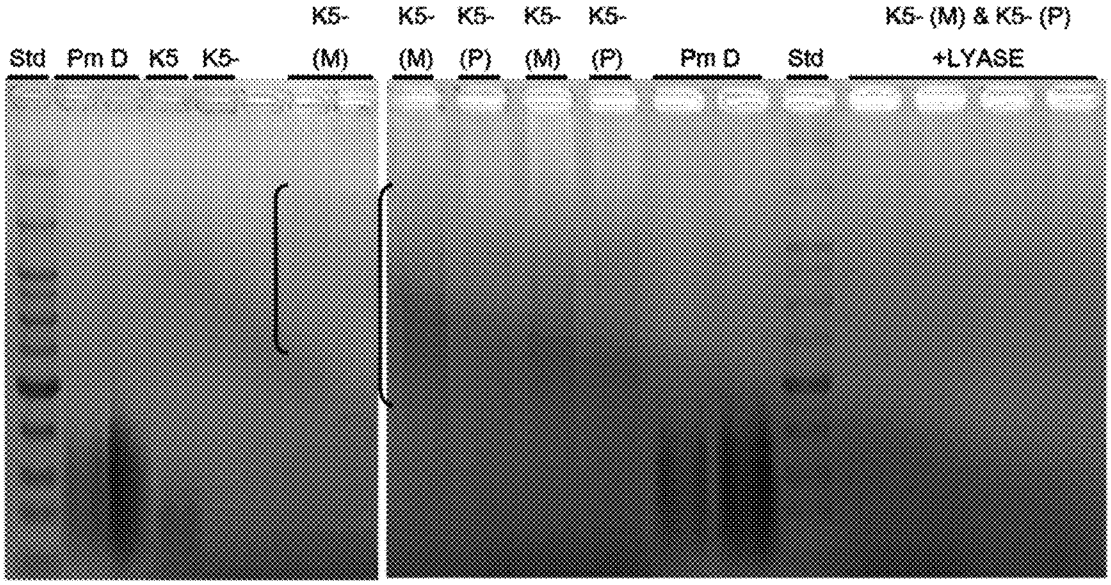
FIG. 5 depicts a gel analysis demonstrating the production of ultra-high molecular weight heparosan polymer in *E. coli* $K5^-$ (in which the kfiA, kfiB, and kfiC genes have been deleted) with either plasmid-borne recombinant PmHS1 gene or the expression plasmid that produces the maltose-binding protein (MBP) PmHS1 fusion protein.

The kfiA, kfiB, and kfiC genes in *E. coli* K5 were deleted, and the resulting strain (K5-) no longer produces the 50-80 kDa heparosan usually produced by K5. The K5-strain was transformed with either pKK223-3/gene-optimized PmHS1 (P) or pMAL-C4e/gene-optimized PmHS1 (M). Cultures of the transformants were induced with IPTG and then grown overnight in either LB. The culture media was then clarified by centrifugation, and the heparosan polymer concentrated by ethanol precipitation. The identity of the heparosan polymer was confirmed by digestion with heparin lyase III (+LYASE). The agarose gel analysis (1×TAE, Stains-All detection) shown in FIG. 5 demonstrated that the construct of the plasmid-borne recombinant gene-optimized PmHS1 gene from *P. multocida* Type D, expressed in *E. coli* K5 with no kfiA, kfiB, or kfiC genes, produced a very high MW heparosan polymer (~2 MDa; band marked with a bracket). Std=SelectHA MegaLadder/SelectHA HiLadder/SelectHA LoLadder (Hyalose LLC) with bands from top to bottom: 6100, 4570, 3050, 1510, 1090, 966, 572, 495, 310, 214, 110, 27 kDa (kDa=1,000 Da; MDa=1,000 kDa).

Thus, the kfiA, kfiB, and kfiC genes are not involved in the production of ultra-high MW heparosan in *E. coli* K5.

Although the foregoing inventive concept(s) has been described in detail by way of illustration and example for purposes of clarity of understanding, it will be obvious to those skilled in the art that certain changes and modifications may be practiced without departing from the spirit and scope thereof, as described in this specification and as defined in the appended claims below.

REFERENCES

The following references, to the extent that they provide exemplary procedural or other details supplementary to those set forth herein, are specifically incorporated herein by reference in their entirety as though set forth herein particular.

1. Burg, K. J., Porter, S., and Kellam, J. F. (2000) Biomaterial developments for bone tissue engineering *Biomaterials* 21, 2347-2359
2. Luo, Y., Kirker, K. R., and Prestwich, G. D. (2000) Cross-linked hyaluronic acid hydrogel films: new biomaterials for drug delivery *J Control Release* 69, 169-184
3. Morra, M. (2005) Engineering of biomaterials surfaces by hyaluronan *Biomacromolecules* 6, 1205-1223
4. Olivier, V., Faucheux, N., and Hardouin, P. (2004) Biomaterial challenges and approaches to stem cell use in bone reconstructive surgery *Drug Discov Today* 9, 803-811
5. Johl, S. S., and Burgett, R. A. (2006) Dermal filler agents: a practical review *Curr Opin Ophthalmol* 17, 471-479
6. Eppley, B. L., and Dadvand, B. (2006) Injectable soft-tissue fillers: clinical overview *Plast Reconstr Surg* 118, 98e-106e
7. Jordan, S. W., and Chaikof, E. L. (2007) Novel thromboresistant materials *J Vasc Surg* 45 Suppl A, A104-115
8. DeAngelis, P. L. (2002) Microbial glycosaminoglycan glycosyltransferases *Glycobiology* 12, 9R-16R
9. DeAngelis, P. L. (2002) Evolution of glycosaminoglycans and their glycosyltransferases: Implications for the extracellular matrices of animals and the capsules of pathogenic bacteria *Anatomical Record* 268, 317-326
10. Jann, K., and Jann, B. (1992) Capsules of *Escherichia coli*, expression and biological significance *Can J Microbiol* 38, 705-710
11. Sugahara, K., and Kitagawa, H. (2002) Heparin and heparan sulfate biosynthesis *IUBMB Life* 54, 163-175
12. Esko, J. D., and Lindahl, U. (2001) Molecular diversity of heparan sulfate *J Clin Invest* 108, 169-173
13. Hardingham, T. E., and Fosang, A. J. (1992) Proteoglycans: many forms and many functions *Faseb J* 6, 861-870
14. Laurent, T. C., and Fraser, J. R. (1992) Hyaluronan *Faseb J* 6, 2397-2404
15. Toole, B. P. (2000) Hyaluronan is not just a goo! *J Clin Invest* 106, 335-336
16. DeAngelis, P. L., Gunay, N. S., Toida, T., Mao, W. J., and Linhardt, R. J. (2002) Identification of the capsular polysaccharides of Type D and F *Pasteurella multocida* as unmodified heparin and chondroitin, respectively *Carbohydr Res* 337, 1547-1552
17. Gorbet, M. B., and Sefton, M. V. (2004) Biomaterial-associated thrombosis: roles of coagulation factors, complement, platelets and leukocytes *Biomaterials* 25, 5681-5703
18. Ma, Z., Mao, Z., and Gao, C. (2007) Surface modification and property analysis of biomedical polymers used for tissue engineering *Colloids Surf B Biointerfaces*
19. Massia, S. P., Holecko, M. M., and Ehteshami, G. R. (2004) In vitro assessment of bioactive coatings for neural implant applications *J Biomed Mater Res A* 68, 177-186
20. Czaja, W. K., Young, D. J., Kawecki, M., and Brown, R. M., Jr. (2007) The future prospects of microbial cellulose in biomedical applications *Biomacromolecules* 8, 1-12

21. Chandy, T., and Sharma, C. P. (1990) Chitosan—as a biomaterial *Biomater Artif Cells Artif Organs* 18, 1-24

22. Allison, D. D., and Grande-Allen, K. J. (2006) Review. Hyaluronan: a powerful tissue engineering tool *Tissue Eng* 12, 2131-2140

23. McKenzie, E., Young, K., Hircock, M., Bennett, J., Bhaman, M., Felix, R., Turner, P., Stamps, A., McMillan, D., Saville, G., Ng, S., Mason, S., Snell, D., Schofield, D., Gong, H., Townsend, R., Gallagher, J., Page, M., Parekh, R., and Stubberfield, C. (2003) Biochemical characterization of the active heterodimer form of human heparanase (Hpa1) protein expressed in insect cells *Biochem J* 373, 423-435

24. Vlodaysky, I., Friedmann, Y., Elkin, M., Aingorn, H., Atzmon, R., Ishai-Michaeli, R., Bitan, M., Pappo, O., Peretz, T., Michal, I., Spector, L., and Pecker, I. (1999) Mammalian heparanase: gene cloning, expression and function in tumor progression and metastasis *Nat Med* 5, 793-802

25. Pikas, D. S., Li, J. P., Vlodaysky, I., and Lindahl, U. (1998) Substrate specificity of heparanases from human hepatoma and platelets *J Biol Chem* 273, 18770-18777

26. Gong, F., Jemth, P., Escobar Galvis, M. L., Vlodaysky, I., Horner, A., Lindahl, U., and Li, J. P. (2003) Processing of macromolecular heparin by heparanase *J Biol Chem* 278, 35152-35158

27. Balazs, E. A. (2004) Viscosupplementation for treatment of osteoarthritis: from initial discovery to current status and results *Surg Technol Int* 12, 278-289

28. Goa, K. L., and Benfield, P. (1994) Hyaluronic acid. A review of its pharmacology and use as a surgical aid in ophthalmology, and its therapeutic potential in joint disease and wound healing *Drugs* 47, 536-566

29. Stern, R. (2004) Hyaluronan catabolism: a new metabolic pathway *Eur J Cell Biol* 83, 317-325

30. DeAngelis, P. L., and White, C. L. (2002) Identification and molecular cloning of a heparosan synthase from *Pasteurella multocida* type D *J Biol Chem* 277, 7209-7213

31. Barzu, T., van Rijn, J. L., Petitou, M., Tobelem, G., and Caen, J. P. (1987) Heparin degradation in the endothelial cells *Thromb Res* 47, 601-609

32. Vann, W. F., Schmidt, M. A., Jann, B., and Jann, K. (1981) The structure of the capsular polysaccharide (K5 antigen) of urinary-tract-infective *Escherichia coli* 010: K5:H4. A polymer similar to desulfo-heparin *Eur J Biochem* 116, 359-364

33. Capila, I., and Linhardt, R. J. (2002) Heparin-protein interactions *Angew Chem Int Ed Engl* 41, 391-412

34. Tammi, M. I., Day, A. J., and Turley, E. A. (2002) Hyaluronan and homeostasis: a balancing act *J Biol Chem* 277, 4581-4584

35. Stern, R., Asari, A. A., and Sugahara, K. N. (2006) Hyaluronan fragments: an information-rich system *Eur J Cell Biol* 85, 699-715

36. Powell, J. D., and Horton, M. R. (2005) Threat matrix: low-molecular-weight hyaluronan (HA) as a danger signal *Immunol Res* 31, 207-218

37. West, D. C., and Kumar, S. (1989) Hyaluronan and angiogenesis *Ciba Found Symp* 143, 187-201; discussion 201-187, 281-185

38. Trochon, V., Mabilat, C., Bertrand, P., Legrand, Y., Smadja-Joffe, F., Soria, C., Delpech, B., and Lu, H. (1996) Evidence of involvement of CD44 in endothelial cell proliferation, migration and angiogenesis in vitro *Int J Cancer* 66, 664-668

39. Scheibner, K. A., Lutz, M. A., Boodoo, S., Fenton, M. J., Powell, J. D., and Horton, M. R. (2006) Hyaluronan fragments act as an endogenous danger signal by engaging TLR2 *J Immunol* 177, 1272-1281

40. Hodson, N., Griffiths, G., Cook, N., Pourhossein, M., Gottfridson, E., Lind, T., Lidholt, K., and Roberts, I. S. (2000) Identification that KfiA, a protein essential for the biosynthesis of the *Escherichia coli* K5 capsular polysaccharide, is an alpha-UDP-GlcNAc glycosyltransferase. The formation of a membrane-associated K5 biosynthetic complex requires KfiA, KfiB, and KfiC *J Biol Chem* 275, 27311-27315

41. Monheit, G. D., and Coleman, K. M. (2006) Hyaluronic acid fillers *Dermatol Ther* 19, 141-150

42. Li, M., Timmons, R. B., and Kinsel, G. R. (2005) Radio frequency plasma polymer coatings for affinity capture MALDI mass spectrometry *Anal Chem* 77, 350-353

43. Su, S. H., Chao, R. Y., Landau, C. L., Nelson, K. D., Timmons, R. B., Meidell, R. S., and Eberhart, R. C. (2003) Expandable bioresorbable endovascular stent. I. Fabrication and properties *Ann Biomed Eng* 31, 667-677

44. Bitter, T., and Muir, H. M. (1962) A modified uronic acid carbazole reaction *Anal Biochem* 4, 330-334

45. Lee, H. G., and Cowman, M. K. (1994) An agarose gel electrophoretic method for analysis of hyaluronan molecular weight distribution *Anal Biochem* 219, 278-287

46. Tracy, B. S., Avci, F. Y., Linhardt, R. J., and DeAngelis, P. L. (2007) Acceptor specificity of the *Pasteurella* hyaluronan and chondroitin synthases and production of chimeric glycosaminoglycans *J Biol Chem* 282, 337-344

47. Deangelis P L, White C L. (2004) Identification of a distinct, cryptic heparosan synthase from *Pasteurella multocida* types A, D, and F. *J Bacteriol.* 186, 8529-32.

What is claimed is:

1. A method for recombinantly producing a high molecular weight heparosan polymer, the method comprising the steps of:

culturing a recombinant host cell containing a nucleotide sequence encoding a polypeptide having heparosan synthase activity under conditions appropriate for the expression of the heparosan synthase, wherein at least one of:

(a) the polypeptide having heparosan synthase activity is at least 90% identical to at least one of SEQ ID NOS: 2, 4, and 6-8, and the nucleotide sequence encoding the polypeptide has been gene-optimized for expression in the recombinant host cell;

(b) the polypeptide having heparosan synthase activity has 1-20 amino acid additions, deletions, and/or substitutions when compared to at least one of SEQ ID NOS: 2, 4, and 6-8, and the nucleotide sequence encoding the polypeptide has been gene-optimized for expression in the recombinant host cell;

(c) the polypeptide is encoded by the nucleotide sequence of at least one of SEQ ID NOS: 9-11;

(d) the polypeptide is encoded by a nucleotide sequence that is at least 90% identical to at least one of SEQ ID NOS: 9-11; and (e) the nucleotide sequence encodes a *Pasteurella* heparosan synthase; and isolating heparosan polymer produced by the heparosan synthase, wherein the isolated heparosan polymer is biocompatible with a mammalian patient and biologically inert within extracellular compartments of a mammalian patient, and wherein the isolated heparosan polymer is represented by the structure (-GlcUA-beta1, 4-GlcNAc-alpha-1,4-)$_n$, wherein n is a positive integer greater than or equal to 2,000.

2. The method of claim 1, wherein the recombinant host cell further comprises at least one gene encoding an enzyme for synthesis of a heparosan sugar precursor, wherein the at least one gene encoding an enzyme for synthesis of a heparosan sugar precursor is selected from the group consisting of a pyrophosphorylase, a transferase, a mutase, a dehydrogenase, and an epimerase, capable of producing UDP-GlcNAc or UDP-GlcUA.

3. The method of claim 1, further comprising at least one of the steps of:

(a) crosslinking the isolated heparosan polymer; and/or (b) covalently and/or non-covalently attaching the isolated heparosan polymer to at least a portion of a surface of a substrate; optionally where the substrate is selected from the group consisting of silica, silicon, semiconductors, glass, polymers, nanotubes, nanoparticles, organic compounds, inorganic compounds, metals, and combinations thereof; optionally wherein at least a portion of the substrate is a metal selected from the group consisting of gold, copper, stainless steel, nickel, aluminum, titanium, thermosensitive alloys, and combinations thereof.

4. The method of claim 1, wherein the recombinant host cell is an *E. coli* recombinant host cell.

5. The method of claim 1, wherein the isolated heparosan polymer is further defined as having a value for n in a range of from about 2,000 to about 17,000.

6. The method of claim 1, wherein the isolated heparosan polymer is substantially not susceptible to mammalian hyaluronidases or heparanases and thereby is not substantially degraded in vivo in extracellular compartments of a mammalian patient.

* * * * *

SEQUENCE LISTING

```
<160> NUMBER OF SEQ ID NOS: 11

<210> SEQ ID NO 1
<211> LENGTH: 1851
<212> TYPE: DNA
<213> ORGANISM: Pasteurella multocida

<400> SEQUENCE: 1

atgagcttat ttaaacgtgc tactgagcta tttaagtcag gaaactataa agatgcacta      60

actctatatg aaaatatagc taaaatttat ggttcagaaa gccttgttaa atataatatt     120

gatatatgta aaaaaaatat aacacaatca aaaagtaata aaatagaaga agataatatt     180
```

-continued

```
tctggagaaa acaaattttc agtatcaata aaagatctat ataacgaaat aagcaatagt    240

gaattaggga ttacaaaaga aagactagga gcccccccctc tagtcagtat tataatgact    300

tctcataata cagaaaaatt cattgaagcc tcaattaatt cactattatt gcaaacatac    360

aataacttag aagttatcgt tgtagatgat tatagcacag ataaaacatt tcagatcgca    420

tccagaatag caaactctac aagtaaagta aaaacattcc gattaaactc aaatctaggg    480

acatactttg cgaaaaatac aggaatttta aagtctaaag gagatattat tttctttcag    540

gatagcgatg atgtatgtca ccatgaaaga atcgaaagat gtgttaatgc attattatcg    600

aataaagata atatagctgt tagatgtgca tattctagaa taaatctaga aacacaaaat    660

ataataaaag ttaatgataa taaatacaaa ttaggattaa taactttagg cgtttataga    720

aaagtattta atgaaattgg tttttttaac tgcacaacca aagcatcgga tgatgaattt    780

tatcatagaa taattaaata ctatggtaaa aataggataa ataacttatt tctaccactg    840

tattataaca caatgcgtga agattcatta ttttctgata tggttgagtg ggtagatgaa    900

aataatataa agcaaaaaac ctctgatgct agacaaaatt atctccatga attccaaaaa    960

atacacaatg aaaggaaatt aaatgaatta aaagagattt ttagctttcc tagaattcat   1020

gacgccttac ctatatcaaa agaaatgagt aagctcagca accctaaaat tcctgtttat   1080

ataaatatat gctcaatacc ttcaagaata aaacaacttc aatacactat tggagtacta   1140

aaaaaccaat gcgatcattt tcatatttat cttgatggat atccagaagt acctgatttt   1200

ataaaaaaac tagggaataa agcgaccgtt attaattgtc aaaacaaaaa tgagtctatt   1260

agagataatg gaaagtttat tctattagaa aaacttataa aggaaaataa agatggatat   1320

tatataactt gtgatgatga tatccggtat cctgctgact acacaaacac tatgataaaa   1380

aaaattaata aatacaatga taaagcagca attggattac atggtgttat attcccaagt   1440

agagtcaaca agtatttttc atcagacaga attgtctata attttcaaaa acctttagaa   1500

aatgatactg ctgtaaatat attaggaact ggaactgttg cctttagagt atctattttt   1560

aataaatttt ctctatctga ttttgagcat cctggcatgg tagatatcta tttttctata   1620

ctatgtaaga aaaacaatat actccaagtt tgtatatcac gaccatcgaa ttggctaaca   1680

gaagataaca aaaacactga gaccttattt catgaattcc aaaatagaga tgaaatacaa   1740

agtaaactca ttatttcaaa caacccttgg ggatactcaa gtatatatcc actattaaat   1800

aataatgcta attattctga acttattccg tgtttatctt tttataacga g              1851


<210> SEQ ID NO 2
<211> LENGTH: 615
<212> TYPE: PRT
<213> ORGANISM: Pasteurella multocida

<400> SEQUENCE: 2

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80
```

-continued

```
Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
```

-continued

```
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu Thr Leu Phe His Glu Phe Gln Asn Arg Asp Glu
                565                 570                 575

Ile Gln Ser Lys Leu Ile Ile Ser Asn Asn Pro Trp Gly Tyr Ser Ser
            580                 585                 590

Ile Tyr Pro Leu Leu Asn Asn Asn Ala Asn Tyr Ser Glu Leu Ile Pro
        595                 600                 605

Cys Leu Ser Phe Tyr Asn Glu
    610                 615


<210> SEQ ID NO 3
<211> LENGTH: 1940
<212> TYPE: DNA
<213> ORGANISM: Pasteurella multocida

<400> SEQUENCE: 3

aacaggggat aaggtcagta aatttaggat gatttttgac taatggataa atacttgaat     60

atccccatgg accgttttcc atgatcagct gagtttgttg ctcatcattg tctcgatatt    120

gatgatagag tgtttcgctg tctctattat cttccgttag ccagtttgct ggtcttgaaa    180

tacaaatctg aagaatatta tttttcttac acaagagaga gaaatagata tcagccatgc    240

ctgaatgggt aaagtcagaa agagaaaatt gattaaagag actgactcta aagctaacag    300

ttcctgtacc taatacattg accgctttgt ctttttccag aggtttatag aagctatata    360

ccagtctatc cgccgaaaaa tatttggtca ttctacttgg aaagagaatg ccgtgtaaac    420

caataaccgc tttatcatcg tattcattca gcttcttgat catcgtattg atgtaatcgc    480

ttggatagat aatgtcatca tcacaggtta tataatatcc atcttgattt ttttcaatca    540

actcttccag taaaatgaat ttgccattat ctctaatgga gttatcttta tctttgcaat    600

gaacaacggt tgctttatta cctaaatttt ttatgaagtc agggatttct acatagccat    660

caagataaat atgaaaatga tcacattgat tttttagtat gccgataata cgtcgtaatt    720

gcgctattct tgagggaata gaacaaatat tgatataaac aggaatctta ggattggaca    780

acttactcat ttcttgtggt actggtaagg catcgtaaat acgagggaat tgaaaaagat    840

ttttgaaatc atgtgaggca gtttcgttat gcatcgcttg aaacagggtt gcataatgtt    900

gtctggtatc agacattttc tgtattatgt tatgattgtc tatccattca accatatcag    960

taaataaaga gttttctctc attgtgttgt agtataacgg caagagtaaa ttttttattt   1020

tttcttttcc ataatatttc gcaattctat gaaaaaactc atcatctgag cctttagtcg   1080

tacaattgaa gaaaccaatt tcttgaaata cttttctgtg catacccaag gttataaaac   1140

ctaatctata atccatatta ttgactttaa tgatatgttg tgtttctggt gctagtcttg   1200

agtatgcaca acgaacagca atagtttctt tattagctaa taatatattt acacatcttt   1260

ctattctttc atgatgacat acatcatcac tatcttgaaa gaaaataatg tcacctttag   1320

attttaatat gcctgtattt ttcgcaaagt aagttcctag gtttgaattt aatctaaata   1380

ctctgacttt gcttgttgta ttcgctattc tcgaggcaat ttcaaatgta ttatccgagc   1440
```

-continued

```
tatcatcatc tacaataata atttctatgt ttttatatgt ttgtaacaat aatgaattaa   1500

tagaagcttc gataaattgc gctgtattgt gagatgtcat gataatactg actaatggat   1560

ttacgctgtt ggtttctttg actaacccta aatcactttt agcgacttca ttatataaat   1620

ctgttattga tgttgtttgc ttatcttttt ctagctttgc ttctaatgct tgattatagg   1680

tatatatttt ttcaaattct tgcagaacca attggagttg ttttaataaa agtttatttt   1740

cgttttcaag ggatgcggat agcggatgtt tactgtcctg ttttgccaat aaagtttgtt   1800

gagaaataat gtctttgttt aaagttgttt ttagactatc aattttattt tgaaaggtgt   1860

tgagttcatt ttctttttca tgttgggggg gatttttagt catttgtttt tgagtcatct   1920

cttttttttct cttcatttca                                               1940
```

```
<210> SEQ ID NO 4
<211> LENGTH: 651
<212> TYPE: PRT
<213> ORGANISM: Pasteurella multocida

<400> SEQUENCE: 4

Met Lys Arg Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
65                  70                  75                  80

Phe Glu Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Val Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205

Asp Ile Ile Phe Phe Gln Asp Ser Asp Asp Val Cys His His Glu Arg
    210                 215                 220

Ile Glu Arg Cys Val Asn Ile Leu Leu Ala Asn Lys Glu Thr Ile Ala
225                 230                 235                 240

Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Arg Lys Val Phe Gln Glu Ile Gly Phe Phe Asn Cys Thr Thr Lys
        275                 280                 285
```

-continued

```
Gly Ser Asp Asp Glu Phe Phe His Arg Ile Ala Lys Tyr Tyr Gly Lys
    290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
                325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
        355                 360                 365

Gln Phe Pro Arg Ile Tyr Asp Ala Leu Pro Val Pro Gln Glu Met Ser
    370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Arg Arg Ile Ile Gly Ile Leu Lys Asn
                405                 410                 415

Gln Cys Asp His Phe His Ile Tyr Leu Asp Gly Tyr Val Glu Ile Pro
            420                 425                 430

Asp Phe Ile Lys Asn Leu Gly Asn Lys Ala Thr Val Val His Cys Lys
        435                 440                 445

Asp Lys Asp Asn Ser Ile Arg Asp Asn Gly Lys Phe Ile Leu Leu Glu
    450                 455                 460

Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
                485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
        515                 520                 525

Phe Tyr Lys Pro Leu Glu Lys Asp Lys Ala Val Asn Val Leu Gly Thr
    530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
                565                 570                 575

Lys Lys Asn Asn Ile Leu Gln Ile Cys Ile Ser Arg Pro Ala Asn Trp
            580                 585                 590

Leu Thr Glu Asp Asn Arg Asp Ser Glu Thr Leu Tyr His Gln Tyr Arg
        595                 600                 605

Asp Asn Asp Glu Gln Gln Thr Gln Leu Ile Met Glu Asn Gly Pro Trp
    610                 615                 620

Gly Tyr Ser Ser Ile Tyr Pro Leu Val Lys Asn His Pro Lys Phe Thr
625                 630                 635                 640

Asp Leu Ile Pro Cys Leu Pro Phe Tyr Phe Leu
                645                 650
```

<210> SEQ ID NO 5
<211> LENGTH: 1854
<212> TYPE: DNA
<213> ORGANISM: Pasteurella multocida

<400> SEQUENCE: 5
atgagcttat ttaaacgtgc tactgagcta tttaagtcag gaaactataa agatgcacta 60

-continued

```
actctatatg aaaatatagc taaaatttat ggttcagaaa gccttgttaa atataatatt    120
gatatatgta aaaaaaatat aacacaatca aaaagtaata aaatagaaga agataatatt    180
tctggagaaa acaaattttc agtatcaata aaagatctat ataacgaaat aagcaatagt    240
gaattaggga ttacaaaaga aagactagga gcccccccctc tagtcagtat tataatgact    300
tctcataata cagaaaaatt cattgaagcc tcaattaatt cactattatt gcaaacatac    360
aataacttag aagttatcgt tgtagatgat tatagcacag ataaaacatt tcagatcgca    420
tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg ttttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagctttcc tagaattcat   1020
gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acataaacac tatgataaaa   1380
aaaattaata aatacaatga taaagcagca attggattac atggtgttat attcccaagt   1440
agagtcaaca agtatttttc atcagacaga attgtctata attttcaaaa acctttagaa   1500
aatgatactg ctgtaaatat attaggaact ggaactgttg cctttagagt atctattttt   1560
aataaatttt ctctatctga ttttgagcat cctggcatgg tagatatcta tttttctata   1620
ctatgtaaga aaaacaatat actccaagtt tgtatatcac gaccatcgaa ttggctaaca   1680
gaagataaca aaaacactga gaccttattt catgaattcc aaaatagaga tgaaatacaa   1740
agtaaactca ttatttcaaa caacccttgg ggatactcaa gtatatatcc attattaaat   1800
aataatgcta attattctga acttattccg tgtttatctt tttataacga gtaa         1854
```

<210> SEQ ID NO 6
<211> LENGTH: 617
<212> TYPE: PRT
<213> ORGANISM: Pasteurella multocida

<400> SEQUENCE: 6

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
```

-continued

```
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480
```

```
Arg Val Asn Lys Tyr Phe Ser Ser Asp Arg Ile Val Tyr Asn Phe Gln
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
        595                 600                 605

Ile Pro Cys Leu Ser Phe Tyr Asn Glu
    610                 615


<210> SEQ ID NO 7
<211> LENGTH: 565
<212> TYPE: PRT
<213> ORGANISM: Pasteurella multocida

<400> SEQUENCE: 7

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
```

-continued

```
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu
                565


<210> SEQ ID NO 8
<211> LENGTH: 538
<212> TYPE: PRT
<213> ORGANISM: Pasteurella multocida

<400> SEQUENCE: 8

Ser Asn Ser Glu Leu Gly Ile Thr Lys Glu Arg Leu Gly Ala Pro Pro
1               5                   10                  15

Leu Val Ser Ile Ile Met Thr Ser His Asn Thr Glu Lys Phe Ile Glu
            20                  25                  30
```

-continued

```
Ala Ser Ile Asn Ser Leu Leu Leu Gln Thr Tyr Asn Leu Glu Val Ile
        35                  40                  45

Val Val Asp Asp Tyr Ser Thr Asp Lys Thr Phe Gln Ile Ala Ser Arg
    50                  55                  60

Ile Ala Asn Ser Thr Ser Lys Val Lys Thr Phe Arg Leu Asn Ser Asn
65                  70                  75                  80

Leu Gly Thr Tyr Phe Ala Lys Asn Thr Gly Ile Leu Lys Ser Lys Gly
                85                  90                  95

Asp Ile Ile Phe Phe Gln Ser Asp Asp Val Cys His His Glu Arg Ile
            100                 105                 110

Glu Arg Cys Val Asn Ala Leu Leu Ser Asn Lys Asp Asn Ile Ala Val
        115                 120                 125

Arg Cys Ala Tyr Ser Arg Ile Asn Leu Glu Thr Gln Asn Ile Ile Lys
    130                 135                 140

Val Asn Asp Asn Lys Tyr Lys Leu Gly Leu Ile Thr Leu Gly Val Tyr
145                 150                 155                 160

Arg Lys Val Phe Asn Glu Ile Gly Phe Phe Asn Cys Thr Thr Lys Ala
                165                 170                 175

Ser Asp Asp Glu Phe Tyr His Arg Ile Ile Lys Tyr Tyr Gly Lys Asn
            180                 185                 190

Arg Ile Asn Asn Leu Phe Leu Pro Leu Tyr Tyr Asn Thr Met Arg Glu
        195                 200                 205

Asp Ser Leu Phe Ser Asp Met Val Glu Trp Val Asp Glu Asn Asn Ile
    210                 215                 220

Lys Gln Lys Thr Ser Asp Ala Arg Gln Asn Tyr Leu His Glu Phe Gln
225                 230                 235                 240

Lys Ile His Asn Glu Arg Lys Leu Asn Glu Leu Lys Glu Ile Phe Ser
                245                 250                 255

Phe Pro Arg Ile His Asp Ala Leu Pro Ile Ser Lys Glu Met Ser Lys
            260                 265                 270

Leu Ser Asn Pro Lys Ile Pro Val Tyr Ile Asn Ile Cys Ser Ile Pro
        275                 280                 285

Ser Arg Ile Lys Gln Leu Gln Tyr Thr Ile Gly Val Leu Lys Asn Gln
    290                 295                 300

Cys Asp His Phe His Ile Tyr Leu Asp Gly Tyr Pro Glu Val Pro Asp
305                 310                 315                 320

Phe Ile Lys Lys Leu Gly Asn Lys Ala Thr Val Ile Asn Cys Gln Asn
                325                 330                 335

Lys Asn Glu Ser Ile Arg Asp Asn Gly Lys Phe Ile Leu Leu Glu Lys
            340                 345                 350

Leu Ile Lys Glu Asn Lys Asp Gly Tyr Tyr Ile Thr Cys Asp Asp Asp
        355                 360                 365

Ile Arg Tyr Pro Ala Asp Tyr Thr Asn Thr Met Ile Lys Lys Ile Asn
    370                 375                 380

Lys Tyr Asn Asp Lys Ala Ala Ile Gly Leu His Gly Val Ile Phe Pro
385                 390                 395                 400

Ser Arg Val Asn Lys Tyr Phe Ser Ser Asp Arg Ile Val Tyr Asn Phe
                405                 410                 415

Gln Lys Pro Leu Glu Asn Asp Thr Ala Val Asn Ile Leu Gly Thr Gly
            420                 425                 430

Thr Val Ala Phe Arg Val Ser Ile Phe Asn Lys Phe Ser Leu Ser Asp
        435                 440                 445

Phe Glu His Pro Gly Met Val Asp Ile Tyr Phe Ser Ile Leu Cys Lys
```

-continued

```
    450                 455                 460

Lys Asn Asn Ile Leu Gln Val Cys Ile Ser Arg Pro Ser Asn Trp Leu
465                 470                 475                 480

Thr Glu Asp Asn Lys Asn Thr Glu Thr Leu Phe His Glu Phe Gln Asn
                485                 490                 495

Arg Asp Glu Ile Gln Ser Lys Leu Ile Ile Ser Asn Asn Pro Trp Gly
            500                 505                 510

Tyr Ser Ser Ile Tyr Pro Leu Leu Asn Asn Asn Ala Asn Tyr Ser Glu
        515                 520                 525

Leu Ile Pro Cys Leu Ser Phe Tyr Asn Glu
    530                 535


<210> SEQ ID NO 9
<211> LENGTH: 1864
<212> TYPE: DNA
<213> ORGANISM: Artificial Sequence
<220> FEATURE:
<223> OTHER INFORMATION: Pasteurella multocida heparosan synthase
      sequence gene-optimized for expression in E. coli

<400> SEQUENCE: 9

ggtaccgagc ctgtttaaac gtgcgaccga actgttcaaa agcggtaact ataaagatgc     60

gctgaccctg tatgaaaata ttgcgaaaat ttatggtagc gaaagcctgg ttaaatataa    120

catcgatatc tgcaagaaaa acattaccca gagcaaaagc aacaaaattg aagaagataa    180

cattagcggt gaaaacaaat ttagcgtgag cattaaagat ctgtataacg aaattagcaa    240

cagcgaactg ggcattacca aagaacgcct gggcgcgccg ccgctggtta gcattattat    300

gaccagccac aacaccgaaa aatttattga agcgagcatc aatagcctgc tgctgcagac    360

ctataacaat ctggaagtga ttgttgtgga tgattatagc accgataaaa cctttcagat    420

tgcaagccgt atcgcaaaca gcaccagcaa agttaaaacc tttcgcctga atagcaacct    480

gggcacctat tttgccaaaa acaccggtat tctgaaaagc aaaggcgata tcattttctt    540

tcaggatagc gatgatgtgt gccatcatga acgcattgaa cgctgtgtga acgcgctgct    600

gagcaataaa gataacattg cggtgcgctg cgcctatagc cgtattaacc tggaaaccca    660

gaacattatc aaagttaacg ataacaaata taaactgggt ctgattaccc tgggcgtgta    720

tcgtaaagtt tttaatgaaa ttggcttttt caattgcacc accaaagcaa gcgatgatga    780

attctatcat cgtattatta aatattatgg caaaaaccgt atcaacaacc tgttcctgcc    840

gctgtattat aacaccatgc gtgaagatag cctgtttagc gatatggtgg aatgggtgga    900

tgaaaataac attaaacaga aaaccagcga tgcgcgccag aactatctgc atgaattcca    960

gaaaattcat aacgaacgta aactgaacga actgaaagaa atcttcagct ttccgcgtat   1020

tcacgatgcg ctgccgatta gcaaagaaat gagcaaactg agcaacccga aaatcccggt   1080

gtatattaac atttgcagca tcccgagccg tattaaacag ctgcagtata ccattggtgt   1140

gctgaaaaac cagtgcgatc attttcatat ctatctggat ggctatccgg aagtgcctga   1200

ttttattaaa aaactgggca acaaagcaac cgttattaac tgccagaaca aaaacgaaag   1260

cattcgtgat aacggcaaat ttattctgct ggaaaaactg attaaagaaa acaaagatgg   1320

ttattatatt acctgcgatg atgatattcg ttatccggcg gattatatta acaccatgat   1380

taagaaaatt aacaaatata acgataaagc ggcgattggc ctgcatggcg ttatcttccc   1440

gagccgcgtg aacaaatatt ttagcagcga tcgtatcgtg tataattttc agaaaccgct   1500

ggaaaatgat accgcggtga atattctggg caccggcacc gttgcgttcc gtgtgagcat   1560
```

ttttaataaa tttagcctga gcgatttcga acatccgggc atggtggata tttattttag 1620
cattctgtgc aagaaaaaca acattctgca ggtttgcatt agccgtccta gcaattggct 1680
gaccgaagat aacaaaaata ccgaaaccct gttccacgaa tttcagaacc gtgatgaaat 1740
ccagagcaaa ctgattatta gcaacaatcc gtggggctat agcagcatct atccgctgct 1800
gaacaacaac gcaaactata gcgaactgat tccgtgcctg agcttttata atgaataagg 1860
atcc 1864

<210> SEQ ID NO 10
<211> LENGTH: 1864
<212> TYPE: DNA
<213> ORGANISM: Artificial Sequence
<220> FEATURE:
<223> OTHER INFORMATION: Pasteurella multocida heparosan synthase
sequence gene-optimized for expression in E. coli

<400> SEQUENCE: 10
ggtaccgagc ctgtttaaac gtgcgaccga actgtttaaa agcggcaact ataaagatgc 60
gctgaccctg tatgaaaaca ttgcgaaaat ttatggcagc gaaagcctgg tgaaatacaa 120
catcgatatc tgcaagaaaa acatcaccca gagcaaaagc aacaaaatcg aagaagataa 180
catcagcggc gaaaacaaat ttagcgtgag cattaaagat ctgtataacg aaattagcaa 240
cagcgaactg ggcattacca aagaacgtct gggcgcgccg ccgctggtta gcattattat 300
gaccagccat aacaccgaaa aatttattga agcgagcatt aacagcctgc tgctgcagac 360
ctataacaac ctggaagtga ttgtggtgga tgattatagc accgataaaa cctttcagat 420
tgcgagccgt attgcgaaca gcaccagcaa agtgaaaacc tttcgtctga acagcaacct 480
gggcacctat tttgcgaaaa acaccggcat tctgaaaagc aaaggcgata ttatcttttt 540
ccaggatagc gatgatgtgt gccatcatga acgtattgaa cgttgcgtga acgcgctgct 600
gagcaacaaa gataacattg cggtgcgttg cgcgtatagc cgtattaacc tggaaaccca 660
gaacattatt aaagtgaacg ataacaaata taaactgggc ctgattaccc tgggcgtgta 720
tcgtaaagtg tttaacgaaa ttggtttctt taactgcacc accaaagcga gcgatgatga 780
attctaccat cgtatcatca aatactacgg caaaaaccgt atcaacaacc tgtttctgcc 840
gctgtactac aacaccatgc gtgaagatag cctgtttagc gatatggtgg aatgggtgga 900
tgaaaacaac attaaacaga aaaccagcga tgcgcgtcag aactatctgc atgaattcca 960
gaaaatccat aacgaacgta aactgaacga actgaaagaa atttttagct ttccgcgtat 1020
tcatgatgcg ctgccgatta gcaaagaaat gagcaaactg agcaacccga aaattccggt 1080
gtatattaac atttgcagca ttccgagccg tattaaacag ctgcagtata ccattggcgt 1140
gctgaaaaac cagtgcgatc attttcatat ttatctggat ggctatccgg aagtgccgga 1200
ttttatcaag aaactgggca acaaagcgac cgtgattaac tgccagaaca aaaacgaaag 1260
cattcgtgat aacggcaaat tcatcctgct ggaaaaactg atcaaagaaa acaaagatgg 1320
ctactacatc acctgcgatg atgatatccg ttatccggcg gattacatca acaccatgat 1380
taagaaaatc aacaaataca acgataaagc ggcgattggc ctgcatggcg tgatttttcc 1440
gagccgtgtg aacaaatatt ttagcagcga tcgtattgtg tataactttc agaaaccgct 1500
ggaaaacgat accgcggtga acattctggg caccggcacc gtggcgtttc gtgtgagcat 1560
ttttaacaaa tttagcctga gcgattttga acatccgggc atggtggata tttattttag 1620
cattctgtgc aagaaaaaca acattctgca ggtgtgcatt agccgtccga gcaactggct 1680

-continued gaccgaagat aacaaaaaca ccgaaaccct gtttcatgaa tttcagaacc gtgatgaaat 1740
tcagagcaaa ctgattatta gcaacaaccc gtggggctat agcagcattt atccgctgct 1800
gaacaacaac gcgaactata gcgaactgat tccgtgcctg agcttttata acgaataagg 1860
atcc 1864

<210> SEQ ID NO 11
<211> LENGTH: 1860
<212> TYPE: DNA
<213> ORGANISM: Artificial sequence
<220> FEATURE:
<223> OTHER INFORMATION: Pasteurella multocida HS sequence gene-
optimized for expression in Bacillus

<400> SEQUENCE: 11
atgggtacct cactgtttaa acgtgctacg gaacttttta aaagcggaaa ctacaaagat 60
gctcttacat tgtacgaaaa catcgccaaa atctatggca gcgaatctct ggttaaatac 120
aacatcgata tctgcaagaa aaatatcacg caatcaaaaa gcaacaaaat cgaagaagat 180
aacatctcag gagaaaacaa attttctgtt tcaatcaaag atttatataa cgaaattagc 240
aattctgaat tgggcatcac aaaagaacgg ttaggcgcac cgcctttggt gtctattatc 300
atgacatcac ataacacgga aaaatttatc gaagccagca tcaactctct gcttttacag 360
acatacaaca accttgaagt catcgttgtg gatgattact ctacagataa aacgtttcaa 420
atcgcttcaa gaatcgccaa ttcaacaagc aaagtaaaaa cgtttcgctt aaacagcaat 480
ttgggcacat actttgctaa aaacacgggc atcttaaaaa gcaaaggaga tatcattttc 540
tttcaggatt ctgatgatgt ctgccatcat gaaagaattg aacgctgtgt aaatgccttg 600
ctgagcaaca aagataatat tgcagtccgt tgcgcgtatt ctcggatcaa cctggaaaca 660
caaaacatca tcaaagtaaa cgataacaaa tacaaattgg gcctgattac gcttggagtt 720
tatcgtaaag tgtttaacga aatcggcttt ttcaattgta caacgaaagc ctctgatgat 780
gaattttacc atagaatcat caaatactat ggaaaaaatc gcattaataa cctgtttctg 840
ccgttgtact acaacacaat gcgtgaagat tcattattta gcgatatggt cgaatgggta 900
gatgaaaaca acatcaaaca aaaaacgtca gatgcacggc agaactactt gcatgaattt 960
caaaaaatcc ataacgaacg taaactgaac gaacttaaag aaatttttag ctttccgaga 1020
attcatgatg cgctgcctat ctcaaaagaa atgtctaaac tttcaaaccc gaaaatccct 1080
gtttacatca acatttgctc aattccgtct cgcatcaaac aattacagta cacaatcgga 1140
gtgttgaaaa accagtgtga tcattttcat atctacttgg atggctatcc ggaagttcct 1200
gattttatca aaaaattggg aaacaaagca acggtgatca actgccaaaa caaaaacgaa 1260
agcatcagag ataacggcaa atttatcctt ttagaaaaat tgatcaaaga aaacaaagat 1320
ggatactaca tcacatgtga tgatgatatt cgctatcctg cggattatat taatacgatg 1380
attaagaaaa ttaacaaata caacgataaa gcagcgatcg gcctgcatgg agttatcttt 1440
ccgtctcgtg tgaacaaata cttttcaagc gatcggatcg tctacaactt tcagaaacct 1500
ttagaaaacg atacagcagt aaacatcttg ggcacaggaa cggtcgcgtt tagagtatca 1560
atctttaaca aattttctct gtcagatttt gaacatccgg gcatggttga tatctacttt 1620
agcatcctgt gcaagaaaaa taacatcctt caagtgtgta tctcaagacc tagcaattgg 1680
ctgacagaag ataacaaaaa cacagaaacg ctttttcatg aatttcaaaa ccgcgatgaa 1740

-continued

```
atccagagca aacttatcat ctctaacaac ccgtggggat attcttcaat ctaccctttg   1800
ctgaacaaca acgcaaacta ctcagaactg atcccgtgtc ttagctttta taacgaataa   1860
```